United States Patent
Hayes et al.

(10) Patent No.: US 9,833,194 B2
(45) Date of Patent: Dec. 5, 2017

(54) PATIENT SUPPORT APPARATUS WITH REMOTE COMMUNICATIONS

(71) Applicant: Stryker Corporation, Kalamazoo, MI (US)

(72) Inventors: Michael Joseph Hayes, Kalamazoo, MI (US); David Terrance Becker, Grand Rapids, MI (US); Annie Désaulniers, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 155 days.

(21) Appl. No.: 14/211,613

(22) Filed: Mar. 14, 2014

(65) Prior Publication Data

US 2014/0259414 A1 Sep. 18, 2014

Related U.S. Application Data

(60) Provisional application No. 61/790,823, filed on Mar. 15, 2013.

(51) Int. Cl.
*A61G 5/02* (2006.01)
*A61B 5/00* (2006.01)
(Continued)

(52) U.S. Cl.
CPC ............ *A61B 5/6892* (2013.01); *A61B 5/002* (2013.01); *A61B 5/1117* (2013.01); *A61B 5/447* (2013.01);
(Continued)

(58) Field of Classification Search
CPC ..................................................... A61G 5/02
(Continued)

(56) References Cited

U.S. PATENT DOCUMENTS

| 5,276,432 A | 1/1994 | Travis |
| 7,477,285 B1 | 1/2009 | Johnson |

(Continued)

FOREIGN PATENT DOCUMENTS

WO 199427544 12/1994

OTHER PUBLICATIONS

PCT International Search Report regarding Application No. PCT/US2014/024672 filed Mar. 12, 2014, a counterpart of U.S. Appl. No. 14/211,613.
(Continued)

*Primary Examiner* — Fredrick Conley
(74) *Attorney, Agent, or Firm* — Warner Norcross & Judd LLP

(57) ABSTRACT

A patient support apparatus includes a computer supported thereon that acts as a thin client for at least one network service available on a remote network to which the patient support apparatus has access. The thin client architecture of the patient support apparatus enables the patient support apparatus to dynamically change its functions, algorithms, features and other aspects more easily. The thin client architecture may be applied to generating alerts, performing maintenance functions, analyzing sensor data—including, but not limited to—weight sensors used to detect weight distributions on the patient support apparatus, implementing patient care protocols, performing patient assessments, accumulating information for billing, and monitoring patient movement. The patient support apparatuses may also function as local WiFi hotspots and/or as software access points to the healthcare network and/or the Internet. One or more Software-as-a-Service applications may run on the patient support apparatus.

28 Claims, 13 Drawing Sheets

(51) Int. Cl.
*A61B 5/11* (2006.01)
*A61G 7/018* (2006.01)
*A61G 7/05* (2006.01)
*A61G 7/012* (2006.01)
*A61G 7/015* (2006.01)
*G08B 21/04* (2006.01)
*G06F 19/00* (2011.01)

(52) U.S. Cl.
CPC ............ *A61B 5/7275* (2013.01); *A61G 7/018* (2013.01); *A61G 7/0524* (2016.11); *G06F 19/3412* (2013.01); *A61B 5/0022* (2013.01); *A61G 7/012* (2013.01); *A61G 7/015* (2013.01); *G06F 19/3418* (2013.01); *G08B 21/0461* (2013.01)

(58) Field of Classification Search
USPC .......... 340/573.1, 524, 13.24, 539.11; 705/2; 5/600, 611
See application file for complete search history.

(56) References Cited

U.S. PATENT DOCUMENTS

| | | |
|---|---|---|
| 7,699,784 B2 | 4/2010 | Wan Fong et al. |
| 8,284,047 B2 | 10/2012 | Collins, Jr. et al. |
| 8,413,271 B2 | 4/2013 | Blanchard et al. |
| 8,618,918 B2 | 12/2013 | Tallent et al. |
| 8,674,826 B2 | 3/2014 | Becker et al. |
| 2002/0196141 A1* | 12/2002 | Boone ................ A61B 5/02055 340/540 |
| 2003/0052787 A1* | 3/2003 | Zerhusen ............ A47B 23/046 340/573.1 |
| 2007/0027714 A1 | 2/2007 | Fenno |
| 2007/0157385 A1* | 7/2007 | Lemire .................. A61G 7/005 5/600 |
| 2007/0174964 A1 | 8/2007 | Lemire et al. |
| 2007/0174965 A1* | 8/2007 | Lemire .................. A61G 7/005 5/600 |
| 2008/0094207 A1* | 4/2008 | Collins, Jr. ........... A61B 5/1115 340/539.12 |
| 2008/0126132 A1 | 5/2008 | Warner et al. |
| 2008/0221466 A1 | 9/2008 | Brauers et al. |
| 2008/0275349 A1* | 11/2008 | Halperin .............. A61B 5/0205 600/484 |
| 2008/0281638 A1* | 11/2008 | Weatherly ............. G06F 19/322 705/3 |
| 2011/0030141 A1 | 2/2011 | Soderberg et al. |
| 2011/0144548 A1 | 6/2011 | Elliott et al. |
| 2012/0223821 A1 | 9/2012 | Collins, Jr. et al. |
| 2012/0289787 A1 | 11/2012 | Kurgan et al. |
| 2013/0205501 A1 | 8/2013 | Robertson et al. |
| 2014/0039351 A1 | 2/2014 | Mix et al. |

OTHER PUBLICATIONS

PCT International Written Opinion egarding Application No. PCT/US2014/024672 filed Mar. 12, 2014, a counterpart of U.S. Appl. No. 14/211,613.

* cited by examiner

PATIENT SUPPORT APPARATUS WITH REMOTE COMMUNICATIONS

CROSS-REFERENCE TO RELATED APPLICATIONS

This application claims priority to U.S. provisional patent application Ser. No. 61/790,823 filed Mar. 15, 2013 by applicants Michael Hayes et al. and entitled PATIENT SUPPORT APPARATUS WITH REMOTE COMMUNICATIONS, the complete disclosure of which is hereby incorporated herein by reference.

BACKGROUND OF THE INVENTION

The present invention relates to patient support apparatuses—such as beds, stretchers, cots, and the like—and more particularly to the electronics and communication systems on board the patient support apparatus.

SUMMARY OF THE INVENTION

The present invention provides systems and methods for improving the functionality, performance, adaptability, servicing, and/or usefulness of patient support apparatuses. In some embodiments, the patient support apparatus includes a computer that acts as a thin client for at least one network service, thereby enabling upgrades, modifications, improvements, and customizations of the one or more functions performed by the patient support apparatus. The network service may provide information, algorithms, data processing, and/or other features for the patient support apparatus that relate to such features as: monitoring patient movement (including turns), providing patient care assessments, implementing a patient care protocol, monitoring maintenance needs, analyzing sensor data, and implementing an exit alert system. In other embodiments, the patient support apparatus includes a platform for supporting at least one Software-as-a-Service (SaaS) application. In still other embodiments, the patient support apparatus is configured to act as a wireless hotspot for providing Internet access to one or more mobile devices, including, but not limited to, other patient support apparatuses, smart phones, computer tablets, and medical devices.

According to one embodiment, a patient support is provided that includes a frame, a support surface, a display, a transceiver, and a computer. The transceiver is adapted to communicate with a remote network. The computer is in communication with the display and the transceiver and is configured to act as a thin client with respect to at least one network service available on the remote network.

According to another embodiment, a patient support apparatus is provided that includes a frame, a support surface, a transceiver, a display, and a computer. The transceiver is adapted to communicate with a remote network. The computer is supported on the patient support apparatus and in communication with transceiver and the display. The computer is further adapted to control at least one function of the patient support apparatus and the computer includes a software platform for supporting at least one software-as-a-service (SaaS) application. The SaaS application is provided by a network service available on the remote network.

In other embodiments, the computer is adapted to run a plurality of thin client applications, wherein a first one of the thin client applications interacts with a first network service available on the remote network, and a second one of the thin client applications interacts with a second network service available on the remote network. Alternatively, the computer may be configured to support a plurality of SaaS applications, at first one of the SaaS applications being provided by a first network service available on the remote network and a second one of the SaaS applications being provided by a second network service on the remote network.

The network service or SaaS application may provide data for performing at least one of the following: assessing a bed sore risk of a patient; assessing a fall risk of a patient; determining when a patient may be about to exit the patient support apparatus; and determining if a patient has turned or not based on sensors positioned on board the patient support apparatus.

In other embodiments, the patient support apparatus includes a plurality of sensors adapted to detect when a patient may be about to exit the patient support apparatus, and the remote network service provides data to the computer for use in processing the outputs from the plurality of sensors. The patient support apparatus alternatively may include a plurality of sensors adapted to provide information indicative of whether a patient has turned or not while positioned on the support surface, and the network service provides data to the computer for use in processing outputs from the plurality of sensors. In some embodiments, the sensors are load cells adapted to detect the weight distribution of the patient on the support surface.

The computer may forward sensor data to the network service for processing and receive processed data back from the network service, wherein the processed data is a result of the processing of the signals received from the computer. The forwarded sensor data may include information generated from a plurality of force sensors. Such information may enable the network service to determine whether or not the patient has turned while positioned on the patient support apparatus, whether a patient may be about to exit from the support surface, and/or whether a patient on the support surface is asleep or awake.

The network service and/or SaaS application may generate billing information based on usage of the patient support apparatus. The network service and/or SaaS application may alternatively provide information relating to how often a patient supported on the patient support apparatus should be turned, and/or other information relating to a patient care protocol.

The network service may communicate with at least one other network service on the remote network. The other network service may be any one or more of the following: an electronic medical records service; a caregiver workflow service; an admission, discharge and tracking (ADT) service; a real time location service; and/or a caregiver communication service.

The network service and/or SaaS application may monitor infection data.

The network service and/or SaaS application may also control at least a portion of the screen space of the display mounted on the patient support apparatus. The network service and/or SaaS may also control other aspects of the patient support apparatus, such as, but not limited to, alerts, movement, settings, and/or communications.

The network service may be adapted to forward one or more algorithms to the patient support apparatus computer that are used to process one or more outputs from sensors positioned on board the patient support apparatus.

In some embodiments, the transceiver is a WiFi transceiver and the remote network is an Ethernet. In other embodiments, the remote network is the Internet.

The patient support apparatus is any of a bed, a stretcher, a cot, a recliner, and/or an operating table. The patient support apparatus may further include an elevation adjustment mechanism adapted to raise and lower the frame, at least one motor adapted to pivot a section of the support surface about a generally horizontal axis, a plurality of side rails coupled to the frame, and a control panel having controls for controlling the elevation adjustment mechanism and the motor. Still further, the patient support apparatus may include a headboard, a footboard, a plurality of wheels, and a brake for selectively locking and unlocking the wheels. The display on the patient support apparatus is, in some embodiments, a touch screen.

In other embodiments, the network service is configurable by one or more employees of the healthcare facility in which the patient support apparatus is positioned such that the employees are able to configure what information is provided to the patient support apparatus by the network service. The network service may provide a list of questions for assessing an aspect of a patient supported on the patient support apparatus. The list of questions may be controllable by one or more employees of the healthcare facility. The patient support apparatus computer receives the list of questions from the network service and displays the list of questions on the display. The list of questions may provide an assessment of a patient's susceptibility to developing bed sores, or an assessment of a patient's fall risk.

A movement counting device may also be positioned on the patient support apparatus. The movement counting device counts the number of times a component on the patient support apparatus moves, and the computer issues a maintenance alert if the number of times the component on the patient support apparatus moves exceeds a threshold. The threshold may be provided by the network service.

An exit detection system is included on the patient support apparatus in some embodiments. The exit detection system includes a controller and a plurality of load cells positioned on the support surface that are adapted to detect weight support on the support surface. The controller calculates a center of gravity of weight positioned on the support surface, and the computer forwards the calculated centers of gravity to the network application. In some embodiments, the computer forwards to the network service the centers of gravity calculated both moments before, and moments after, a patient exits the patient support.

In other embodiments, the SaaS application determines whether a patient has turned or not while positioned on the support surface, based on the outputs from a plurality of sensors on the patient support apparatus. Alternatively, or additionally, the SaaS application may determine whether a patient is about to exit from the support surface, or whether a patient on the support surface is asleep or awake. Still further, the SaaS application may indicate how often a patient supported on the patient support apparatus should be turned, or it may monitor infection data, or it may provide a list of questions for assessing an aspect of a patient supported on the patient support apparatus. When providing such a list, the questions may be controllable by the employees of the healthcare facility, and the list is displayable on the patient support apparatus display. The list of questions may relate to a patient's susceptibility to developing bed sores, or a patient's fall risk, or to other aspects of a patient.

The SaaS, in some embodiments, controls at least one circumstance under which the computer should issue an alert.

According to another embodiment, a patient support apparatus is provided that includes a frame, a support surface, first and second actuators, and a controller. The first and second actuators are adapted to move first and second components on the patient support apparatus, respectively. The controller controls the first and second actuators and counts the number of times the first actuator is actuated and the number of times the second actuator is actuated. The controller further compares the first count to a first threshold and the second count to a second threshold. If either the first count exceeds the first threshold, or the second count exceeds the second threshold, the controller issues a maintenance alert.

The maintenance alert may be forwarded via a transceiver to a network service available on a remote network. The remote network may be a local area network within the healthcare facility, or multiple buildings of the healthcare facility, or it may be a wide area network, or it may be the Internet. The first actuator may be one of a lift actuator adapted to raise and lower the frame, a tilt actuator for changing a tilt of a pivotable section of the support surface, or a brake actuator for turning on and off a brake on the patient support apparatus. The first and/or second thresholds may be received by the controller from the remote network.

A third actuator may be included on the patient support apparatus that is adapted to move a third component on the patient support apparatus, wherein the controller totals a number of times the third actuator is actuated and issues the maintenance alert if the third number exceeds the third threshold. The controller may be a computer that includes a software platform for supporting at least one software-as-a-service (SaaS) application, wherein the SaaS application compares the first, second, and third numbers to the first, second, and third thresholds, respectively.

The controller may forward the first and second numbers to the network service. The network service may be adapted to gather the first and second numbers from a population of patient support apparatuses, analyze the first and second numbers, and use the analysis for determining the first and second thresholds.

The maintenance alert may be displayed on the display mounted on the patient support apparatus.

According to another embodiment, a patient support apparatus is provided that includes a frame, a support surface, a display, a transceiver, and a computer. The transceiver is adapted to communicate with a remote network. The computer is in communication with the transceiver and configured to act as a wireless software access point for the remote network for devices positioned within communication range of the computer.

The transceiver may follow the standards of IEEE 802.11, or it may communicate using other communication standards. The patient support apparatus may also include a second transceiver different from the first transceiver wherein the second transceiver is adapted to communicate with the computer and at least one device so that the at least one device can use the computer as a software access point. The second transceiver may be a Bluetooth transceiver.

The devices which may communicate the wireless software access point include other patient support apparatuses, smart phones, computer tablets, and/or personal computing devices. The computer configured to act as a wireless software access point may be adapted to provide Internet access to one or more of the devices.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and is capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE EMBODIMENTS

Figure 1:
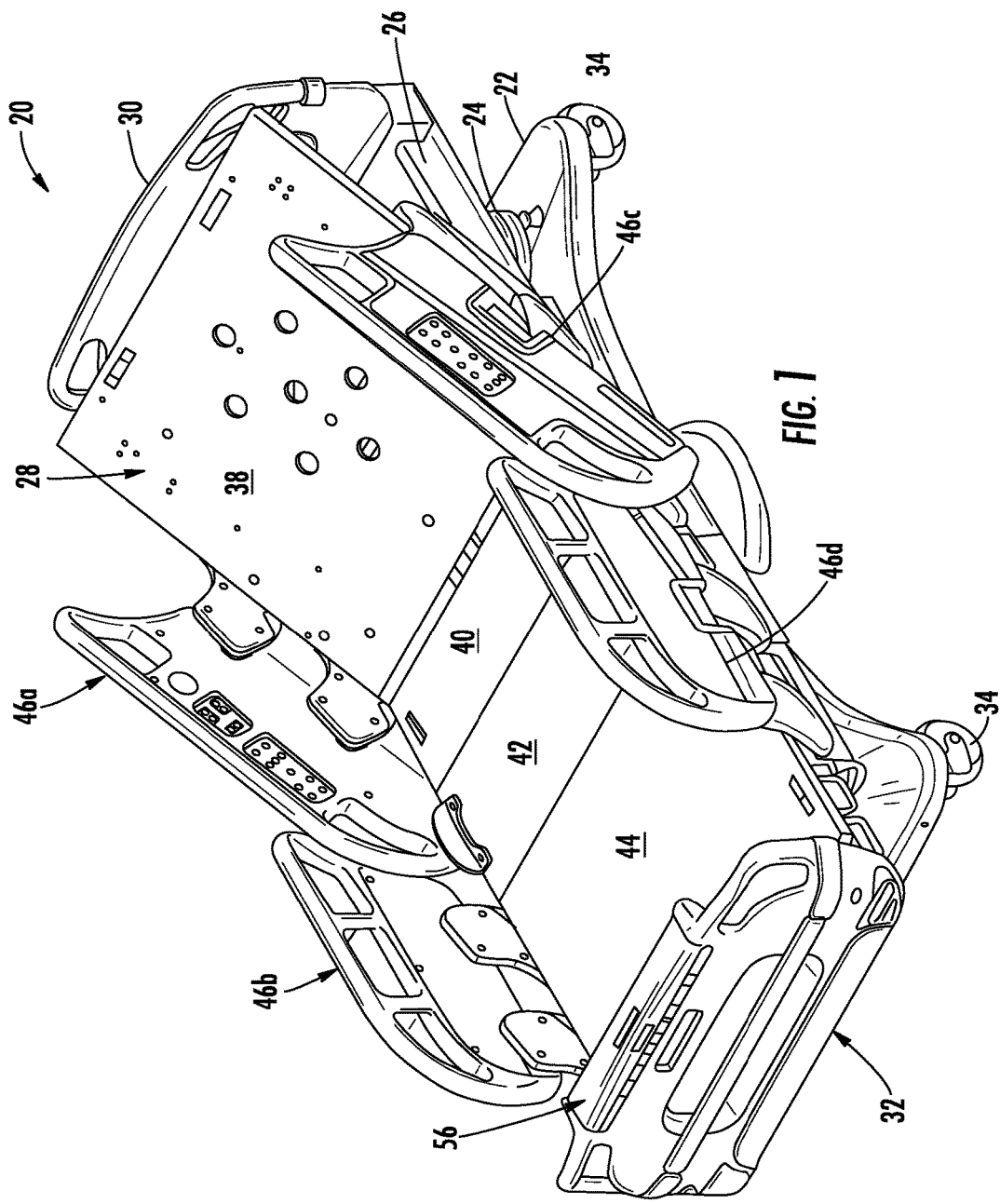
FIG. 1 is a perspective view of an illustrative patient support apparatus that is able to implement any one or more of the various features of the present invention.

The inventive features, functions, and systems described herein are applicable to patient support apparatuses, such as beds, cots, stretchers, operating tables, recliners, and the like. FIG. 1 shows an illustrative patient support apparatus 20—in this case a hospital bed—that may incorporate any one or more of the features, functions, and/or system described herein.

More particularly, FIG. 1 illustrates a patient support apparatus 20 that includes a base 22, a pair of elevation adjustment mechanisms 24, a frame or litter assembly 26, a patient support surface or deck 28, a headboard 30, and a footboard 32. Base 22 includes a plurality of wheels 34 that can be selectively locked and unlocked so that, when unlocked, patient support apparatus 20 is able to be wheeled to different locations. Elevation adjustment mechanisms 24 are adapted to raise and lower frame 26 with respect to base 22. Elevation adjustment mechanisms 24 may be hydraulic actuators, electric actuators, or any other suitable device for raising and lowering frame 26 with respect to base 22. In some embodiments, elevation adjustment mechanisms 24 operate independently so that the orientation of frame 26 with respect to base 22 may also be adjusted.

Frame 26 provides a structure for supporting patient support surface 28, headboard 30, and footboard 32. Patient support surface 28 provides a surface on which a mattress, or other soft cushion, is positionable so that a patient may lie and/or sit thereon. Patient support surface 28 is made of a plurality of sections, some of which are pivotable about generally horizontal pivot axes. In the embodiment shown in FIG. 1, patient support surface 28 includes a head section 38, a seat section 40, a thigh section 42, and a foot section 44. Head section 38, which is also sometimes referred to as a Fowler section, is pivotable between a generally horizontal orientation (not shown in FIG. 1) and a plurality of raised positions (one of which is shown in FIG. 1). Thigh section 42 and foot section 44 may also be pivotable in some embodiments.

In addition to the aforementioned components, patient support apparatus 20 includes four side rails: a right head side rail 46a, a right foot side rail 46b, a left head side rail 46c and a left foot side rail 46d. Side rails 46 are be movable between a raised position and a lowered position. In the configuration shown in FIG. 1, all four of the side rails 46 are raised.

The physical construction of any of base 22, elevation adjustment mechanisms 24, frame 26, patient support surface 28, headboard 30, footboard 32, and/or side rails 46 may be the same as disclosed in commonly assigned, U.S. Pat. No. 7,690,059 issued to Lemire et al., and entitled HOSPITAL BED, the complete disclosure of which is incorporated herein by reference; or as disclosed in commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosure of which is also hereby incorporated herein by reference; or as embodied in the commercially available S3 bed sold by Stryker Corporation of Kalamazoo, Mich., and document in the Stryker Maintenance Manual for Stryker's MedSurg Bed, Model 3002 S3, (doc. 3006-109-002 Rev D), published in 2010, the complete disclosure of which is also hereby incorporated herein by reference. The construction of any of base 22, elevation adjustment mechanisms 24, frame 26, patient support surface 28, headboard 30, footboard 32 and/or side rails 46 may also take on forms different from what is disclosed in these documents.

Figure 2:
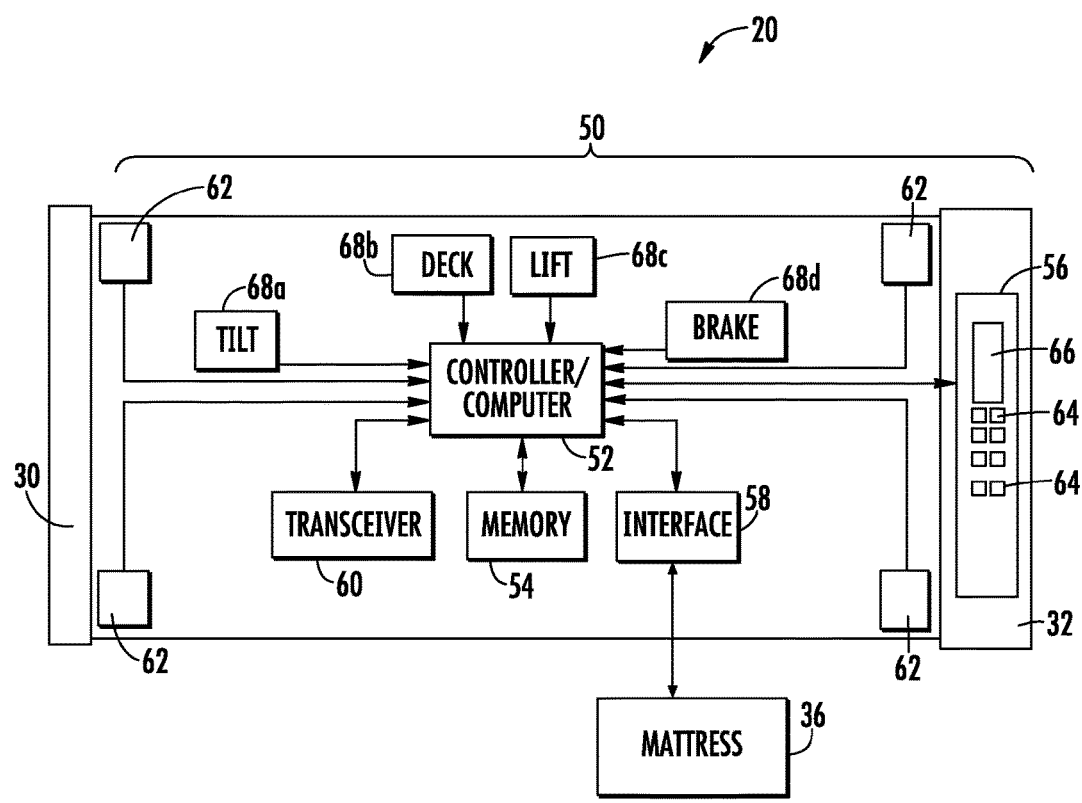
FIG. 2 is a plan view diagram of a control system according to one embodiment that may be implemented into various patient support apparatuses, such as, but not limited to, the one of FIG. 1.

FIG. 2 illustrates a plan view diagram of a control system 50 for patient support apparatus 20. Control system 50 includes a computer or controller 52, a memory 54 in communication with the controller 52, a user interface 56, at least one sensor or device interface 58, at least one transceiver 60, and four force sensors or load cells 62. In the embodiment shown in FIG. 2, control system 50 further includes a plurality of actuators 68, such as a tilt actuator 68a, a deck actuator 68b, a lift actuator 68c, and a brake actuator 68d. Other actuators may also be included.

The components of control system 50 communicate with each other using conventional electronic communication techniques. In one embodiment, controller 52 communicates with memory 54, user interface 56, and load cells 62 using I-squared-C communications. Other types of serial or parallel communication can alternatively be used. In some other embodiments, different methods may be used for different components. For example, in one embodiment, controller 52 communicates with user interface 56 via a Controller Area Network (CAN) or Local Interconnect Network (LIN), while it communicates with memory 54, actuators 68, and load cells 62 using I squared C. Still other variations are possible.

User interface 56 includes a plurality of buttons 64 that a caregiver presses in order to control various features of the patient support apparatus, such as, but not limited to, raising and lowering the height of frame 26 via lift actuators 68a and/or 68c, pivoting one or more of support surface sections 28 via one or more deck actuators 68b, turning on and off a brake (not shown) via brake actuator 68d, controlling a scale system integrated into the patient support apparatus, controlling an exit alert system integrated into the support apparatus 20, and/or controlling other features of the patient support apparatus 20. User interface 56 further includes a display 66 integrated therein. Display 66 is a touchscreen display capable of displaying text and/or graphics and sensing the location that a user's finger touches the display, although it will be understood that display 66 could be modified to be a normal LCD display without touchscreen capabilities that use hard or soft buttons to interact therewith, or still other types of displays.

Controller/computer 52 includes one or more microcontrollers, microprocessors, and/or other programmable electronics that are programmed to carry out the functions described herein. It will be understood that controller 52 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions on patient support apparatus 20, or they may reside in a common location on patient support apparatus 20. When physically distributed, the components may communicate using any suitable serial or parallel communication protocol, such as, but not limited to, CAN, LIN, Firewire, I-squared-C, RS-232, RS-485, etc.

Force sensors 62 are, in some embodiments, any conventional load cells, or similar force measuring sensors, that are positioned to detect the amount of downward force exerted by patient support deck 28, and any objects, patient(s), and/or other persons that are exerting downward forces on support deck 28, whether due to gravity or due to other causes. In some embodiments, the force sensors 62 may be configured so that, in addition to downward forces, they are also able to detect forces exerted in generally horizontal directions (both laterally and longitudinally).

When implemented as load cells, the physical arrangement of force sensors 62 may take on a conventional arrangement, such as those found in a variety of different conventional hospital beds. For example, in one embodiment, the position and physical construction of load cells 62 are the same as that found in the S3® bed sold by Stryker Corporation of Kalamazoo, Mich. These physical details are described in detail in the Stryker Maintenance Manual for Stryker's MedSurg Bed, Model 3002 S3, (doc. 3006-109-002 Rev D), published in 2010, the complete disclosure of which has already been incorporated herein by reference.

Controller 52 is in communication with each of four load cells 62 and receives the outputs from load cells 62. Load cells 62 are positioned adjacent each corner of the patient support surface 28 and cumulatively sense the entire weight of a patient, other person, and/or objects positioned on the patient support surface 28. In one arrangement, the load cells are positioned such that one load cell 62 is positioned adjacent each corner of a load frame (not shown), and the load cells 62 detect forces exerted by a patient support frame upon the load frame (through the load cells). While the construction of the load frame and patient support frame may vary, one example is disclosed in the commonly assigned U.S. Pat. No. 7,690,059 mentioned above and incorporated herein by reference. Another example is disclosed in the Stryker Maintenance Manual for the Model 3002 S3 MedSurg Bed, which has also already been incorporated herein by reference. Other constructions of the frames and positions of the load cells may also be used.

Transceiver 60 is used by controller 52 for forwarding selected information from control system 50 to other devices, such as a healthcare facility computer network 72 (FIG. 3), or another recipient. Healthcare facility computer network 72 is often, though not necessarily always, an Ethernet, and it will be understood that computer network 72 can take on other forms. In one embodiment, transceiver 60 is a WiFi radio transmitter and receiver that is capable of communicating with a wireless access point 88 (FIG. 3) of the hospital network 72 in accordance with IEEE 802.11 standards, or in accordance with other standards. More specific uses of transceiver 60 are discussed below.

It will be understood by those skilled in the art that use of the term "transceiver" throughout this specification is not intended to be limited to devices in which a transmitter and receiver are necessarily within the same housing, or share some circuitry. Instead, the term "transceiver" is used broadly herein to refer to both structures in which circuitry is shared between the transmitter and receiver, and transmitter-receivers in which the transmitter and receiver do not share circuitry and/or a common housing. Thus, the term "transceiver" refers to any device having a transmitter component and a receiver component, regardless of whether the two components are a common entity, separate entities, or have some overlap in their structures.

Interface 58 is used to communicate with one or more electronic devices that are positioned on, or in the vicinity of, patient support apparatus 20. As shown in FIG. 2, interface 58 is configured to communicate with a mattress 36 that is positionable on top of patient support deck 28. Mattress 36 may be a mattress of the type disclosed in commonly assigned U.S. patent application Ser. Nos. 61/696,819 and 61/697,010, entitled INFLATABLE MATTRESS AND CONTROL METHODS and PATIENT SUPPORT, respectively, both of which were filed on Sep. 5, 2012, the complete disclosures of both of which are hereby incorporated herein by reference. Such mattresses include a plurality of inflatable bladders whose inflation pressure is controllable by one or more controllers contained with the mattress. The mattress may further include a plurality of sensors used for detecting information about the status of the mattress, such as, but not limited to, one or more depth sensors, fluid pressure sensors, temperature sensors, patient interface pressures sensors, and/or humidity sensors.

In some embodiments, interface 58 is a Controller Area Network connection that communicates with mattress 36, while in other embodiments, interface 58 takes on other forms. In one embodiment, interface 58 is a wireless connection, such as that disclosed in commonly assigned U.S. patent application Ser. No. 13/296,656 filed Nov. 15, 2011 by applicants Guy Lemire et al. and entitled PATIENT SUPPORT WITH WIRELESS DATA AND/OR ENERGY TRANSFER, the complete disclosure of which is hereby incorporated herein by reference.

In some embodiments, interface 58 may be used to communicate with a flexible pressure sensing mat (not shown), either in addition to, or in lieu of, mattress 36. Such flexible pressure sensing mats are positioned on top of, underneath, or integrated into, mattress 36. Such pressure sensing mats are used to detect the interface pressures between the patient and the support surface the patient is positioned on, and can be useful for monitoring such pressures so as to avoid the development, or potential development, of bed sores. In one embodiment, a flexible pressure sensing mat of the type disclosed in commonly assigned PCT patent application serial number PCT/US12/27402, filed Mar. 2, 2012 by Stryker Corporation, and entitled SENSING SYSTEM FOR PATIENT SUPPORTS, the complete disclosure of which is hereby incorporated herein by reference. Such a flexible pressure sensing mat may forward pressure information, including but not limited to, a patient interface pressure distribution map, to controller 52, and/or any other information that is detectable by the flexible pressure sensing mat (such as, but not limited to, patient heart rate, patient respiration rate, patient position, patient orientation, patient movement—including patient turns, and other information).

In still other embodiments, control system 50 may include more than one interface 58, and each interface 58 may be of the same or different type (e.g. some may be wired, some may be wireless, or they both may be wired or wireless but use different communication protocols). In one embodiment, control system 50 includes a near field communications transceiver that communicates in any of the manners, and with any of the devices, disclosed in commonly assigned U.S. patent application Ser. No. 13/802,992, filed Mar. 14, 2013 by applicants Michael Hayes et al, and entitled COMMUNICATION SYSTEMS FOR PATIENT SUPPORT APPARATUSES, the complete disclosure of which is hereby incorporated herein by reference. Such a near field communications transceiver can be used for establishing associations between patient support apparatus 20 and other objects (e.g. medical devices, mattress 36, patients or caregivers wearing near field ID tags, or other items).

Such associations are forwarded to controller 52. In addition to near field communications, interface 58 may also carry out far field communications using one or more transceivers that are separate from transceiver 60. Such separate transceivers typically communicate using a separate communications protocol than that of transceiver 60. For example, in one embodiment, transceiver 60 using WiFi communications, while the one or more transceivers of interface 68 use Bluetooth and/or ZigBee communications, or other protocols.

Interface 58 may also be configured to communicate with other devices, such as any of the devices disclosed in commonly assigned U.S. patent application Ser. No. 13/570,934 filed Aug. 9, 2012, by applicants Michael Hayes et al. and entitled PATIENT SUPPORT APPARATUS WITH IN-ROOM DEVICE COMMUNICATION, the complete disclosure of which is hereby incorporated herein by reference. When so configured, interface 58 forwards data from the devices it is in communication with to controller 52. Such devices include, but are not limited to, hand washing stations, medical devices, and patient and/or caregiver ID tags. The forwarded information includes associations with, and/ or identifications of, medical devices, caregiver and/or patient identifications, and information about the use or lack of use of handwashing stations.

Controller 52 is configured to create a software environment in which one or more thin client applications are able to operate. Such thin client applications communicate with one or more network services 76 (FIG. 3), which are available on one or more remote networks, such as healthcare facility network 72 and/or the Internet 74. Controller 52 is therefore able to support one or more thin client applications 78 where a substantial portion of the computational workload carried out by the application is done remotely via one or more network services 76. The term "thin client" as used herein shall be given its ordinary and accustomed meaning in the field of computer science and software. In general, a thin client refers to a computer or computer program which depends substantially on another computer or, in this case, one or more network services 76, to fulfill its programmed computational functions.

Although controller 52 is configured to create a thin client software environment, controller 52 does not, in at least some embodiments, exclusively support thin client applications. That is, in some embodiments, controller 52 is configured to support both fat and thin client applications, as well as applications that are purely local. Controller 52, however, is configured such that at least one software application can be supported thereon as either a thin client or a fat client, while at least one other software application is supported thereon that is purely local.

In still other embodiments, separate controllers 52 may be implemented for the different software environments. That is, in one embodiment, a controller 52 may support thin client applications exclusively, while another controller supports fat client applications exclusively, while one or more additional controllers support purely local applications.

Examples of the various thin client, thick client, and local applications that may operate via controller 52 will be discussed in greater detail below, but such applications include any one or more of the following: patient assessment applications (e.g. assessing a patient's risk of falls, assessing a patient's risk of bed sores, etc.); sensor monitoring and/or data collection applications (e.g. gathering load cells outputs—such as patient position, center of gravity, weight, weight distribution, patient movement, etc.—gathering pressure mat outputs, gathering vital sign readings, gathering data from medical devices associated with support apparatus 20 and/or the patient assigned to the support apparatus 20); maintenance monitoring/scheduling applications (e.g. monitoring the actual usage of various components on support apparatus 20 for maintenance purposes); billing applications (e.g. patient usage of support apparatus 20 features, medical device usage, patient presence on support apparatus 20); and/or patient care protocol management applications (e.g. defining, implementing, and/or monitoring of patient care protocols, such as protocols for preventing patient falls, protocols for preventing bed sores, protocols for turning patients, protocols for preventing ventilator-associated-pneumonia (VAP), protocols for containing or reducing infections, etc.).

Including one or more thin or thick client applications operable on controller 52 offers a variety of advantages over traditional patient support apparatuses. Conventional patient support apparatuses typically include one or more computers or controllers that carry out various control functions or protocol features purely locally. While some conventional patient support apparatuses are capable of forwarded information to a server on a remote network, the software carrying this out is purely local. That is, such conventional patient support apparatuses do not include any applications whose features, functions, algorithms, or other computational aspects are carried out at least partially remotely. By having purely local software or applications, conventional patient support apparatuses have features that are generally standard from one healthcare facility to another, are difficult to upgrade, cannot be custom tailored to healthcare facilities, and/or do not easily allow new applications to be added. As will be explained in greater detail below, controller 52's support of thin and thick client applications enables healthcare institutions that purchase patient support apparatus 20 to more easily custom tailor the controls on the patient support apparatus 20, add new functions or features, automatically follow improved algorithms, and adapt more easily to changing user requirements.

Figure 3:
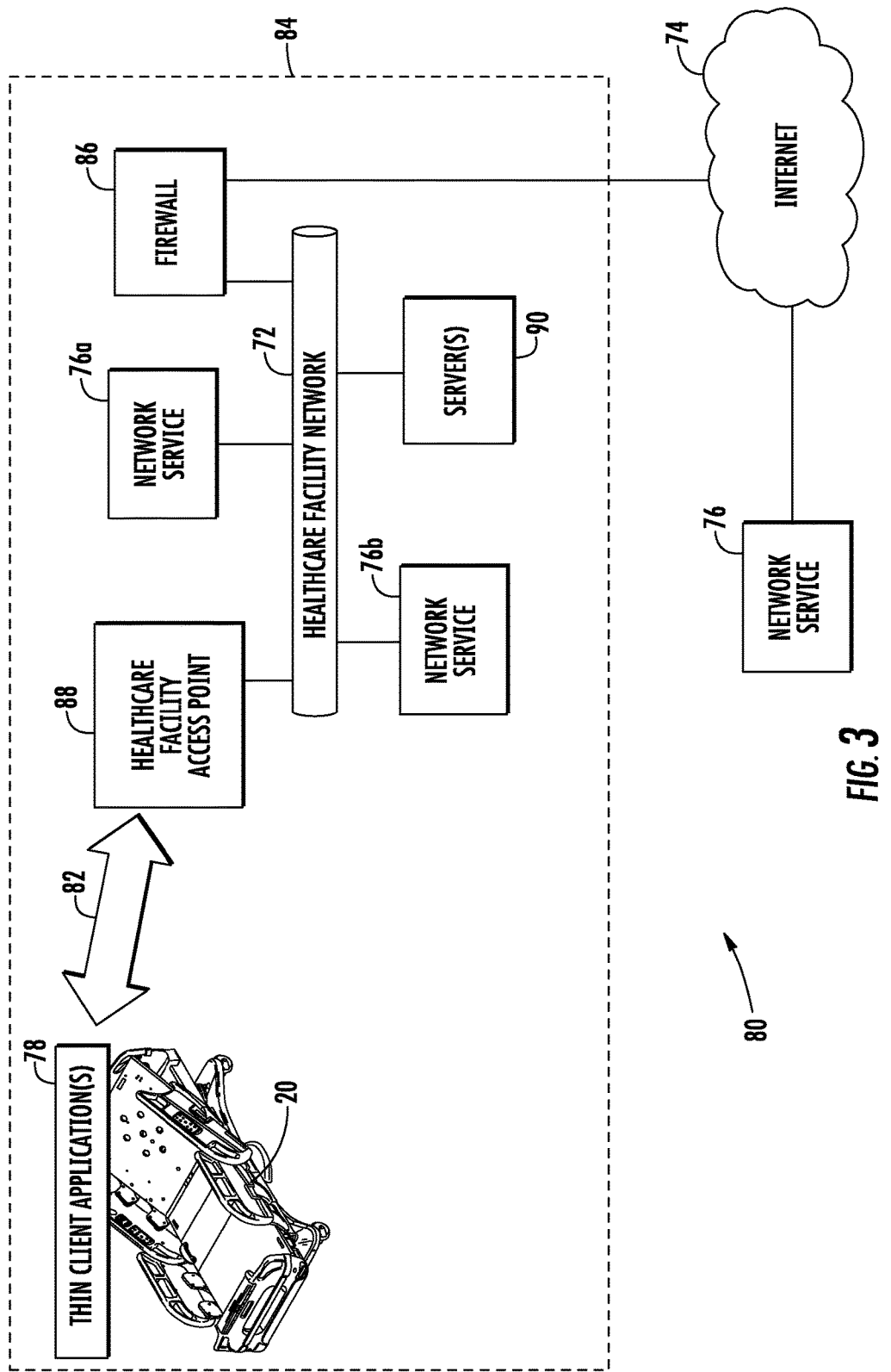
FIG. 3 is a diagram of an illustrative layout of a patient support apparatus communication system.

FIG. 3 illustrates one example of a patient support apparatus software infrastructure layout or configuration 80 that may be implemented by a healthcare facility 82 using one or more patient support apparatuses 20. It will be understood that infrastructure layout 80 is merely an illustrative example of one environment in which patient support apparatus 20 may be implemented, and that various other configurations are possible. Layout 80, however, is provided herein for purposes of explaining various aspects of the invention.

Patient support apparatus software infrastructure layout 80 includes one or more patient support apparatuses 20 that have one or more thin client applications 78 operable thereon. The thin client applications 78 are in electrical communication with one or more network services 76 that are supported on a remote network. The remote network refers to one or more healthcare facility networks 72 positioned within a healthcare facility 84, or one or more networks positioned outside the healthcare facility 84, such as, but not limited to, the Internet 74. It will be understood by those skilled in the art that the term "healthcare facility" will refer not only to an individual building in which patient support apparatuses 20 are positioned, but also collections of buildings (such as are commonly found on a hospital campus). Still further, it will be understood that healthcare facility network 72 refers not only to a Local Area Network that is positioned within a single healthcare facility 84, but also Wide Area Networks that may connect together multiple healthcare facilities 84 that are located in different geographical areas.

Thin client application 78 communicates with the remote network 72 by way of a communications link 82. Communications link 82, in one embodiment, is a wireless communications link that links together transceiver 60 with a wireless access point 88 of the healthcare facility network 72. In one embodiment, communications link 82 is a WiFi communications link and healthcare facility network is an Ethernet. In other embodiments, communications link 82 may be a wired communications link between transceiver 60 and healthcare network 72. Such a wired connection may be carried out by an Ethernet cable, a serial cable, or by other cables. In still other embodiments, communications link is a wireless link that, in some instances, is carried out through the use of one or more mesh networks that patient support apparatuses 20 are part of.

As shown in FIG. 3, patient support apparatus 20 runs at least one thin client application 78 that is dependent upon a network service 76 for carrying out one or more of its full functionality. This is not meant to suggest that thin client application 78 must be in communication with network 72 and its associated network service 76 at all times, but rather that communication is at least periodically required for thin client application 78 to carry out all of its designed functionality. As was noted above, the specific thin client application(s) 78, can vary and include, but are not limited to, patient assessment applications, sensor monitoring and/or data collection applications, maintenance monitoring/scheduling applications, billing applications, patient care protocol management applications, and other applications that relate to patient support apparatus 20, or devices in communication with patient support apparatus 20.

The network service 76 that the thin client application 78 interacts with also does not need to be directly coupled to healthcare facility network 72. For some thin client applications 78, the network service 78 may reside outside the healthcare facility 84, such as one that is available through the Internet 74. In order for the thin client application 78 to communicate with such an Internet application 76, the application 78 will typically have to tunnel through a healthcare facility firewall 86 maintained by the IT department of the particular healthcare facility 84 in which the patient support apparatus 20 is located. Because such tunneling may be impeded by firewall 86 (either on the outbound journey and/or the inbound journey), it may be advantageous for certain thin client applications to have their corresponding network service 76 located on the client side of the firewall 86.

Depending upon the specific network service 76 supported on the healthcare facilities network 72, the network service 76 may interact with one or more servers 90 that are also located on, or otherwise accessible by, the network 72. Such servers 90 include, but are not limited to, the following: an electronic medical (EMR) server; an admission, discharge and transfer (ADT) server; a work flow server; a remote alerting server; and/or one or more nurse's station servers. The EMR server typically contains medical information about the particular patient assigned to a particular patient support apparatus 20. The ADT server typically includes information regarding a patient's identification, location, and status within a healthcare facility, and may contain information that enables a network service 76 to determine which patient is presently occupying a particular support apparatus 20, (which can enable the service 76 to know which information is relevant in the EMR server). The work flow server typically contains information identifying health care personnel, including which caregivers are assigned to which patients. One or more network services 76 may access this information to in order to determine which caregivers should be notified of any alerts issued by the patient support apparatus 20, or the thin client application 78. The remote alerting server typically controls alerts that are issued to wireless devices carried by hospital personnel. Such wireless devices include cell phones, WIFI devices, pagers, computer tablets, personal digital assistants (PDAs), or other structures.

Although the aforementioned servers 90 are often found in a typical hospital setting, it will be understood that the specific servers 90 on a particular healthcare facility's network 72 will vary from facility to facility and will depend upon the specific IT system within a given healthcare facility.

In some embodiments, a patient support apparatus 20 will support multiple thin client applications 78 wherein each thin client application 78 communicates with a different network service 76. Thus, for example, in the layout 80 shown in FIG. 3, a first thin client application 78 may interact with a first network service 76a, while a second thin client application 78 running on the same patient support apparatus 20 as the first thin client application 78 will interact with a second network service 76b.

Figure 4:
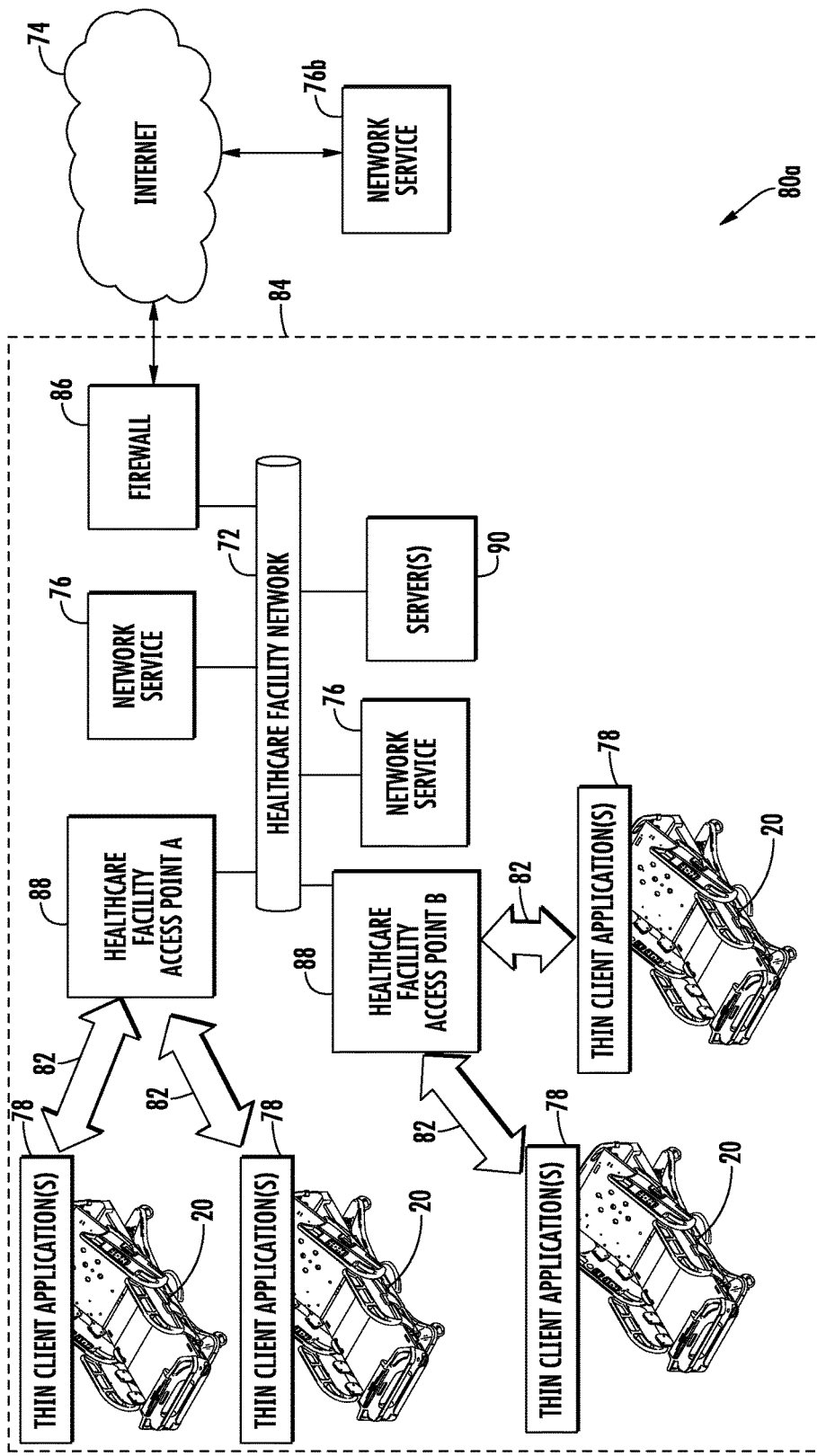
FIG. 4 is a diagram of another illustrative layout of a patient support apparatus communication system showing multiple patient support apparatuses running thin client applications and utilizing multiple access points.

FIG. 4 illustrates another example of a patient support apparatus software infrastructure layout 80a that can be implemented with one or more patient support apparatuses 20 at a healthcare facility 84. Those components that are the same as those found in layout 80 are labeled with the same reference number and operate in the same manner as has been previously described. Those components that are not found in layout 80 are identified with a new reference number.

Layout 80a differs from layout 80 in that layout 80a includes a plurality of patient support apparatuses 20 that are in communication with healthcare facility network 72. Further, layout 80a shows a healthcare facility network 72 having multiple network access points 88. A first set of patient support apparatuses 20 communicate with healthcare network 72 via a first one of the access points 88, while a second set of patient support apparatuses 20 communicate with the healthcare network 72 via a second one of the access points. In many healthcare facilities, there may be more than two access points 88, and a given thin client application 78 on a particular patient support apparatus 20 may communicate with different access points 88 as it moves throughout the healthcare facility 84.

Figure 5:
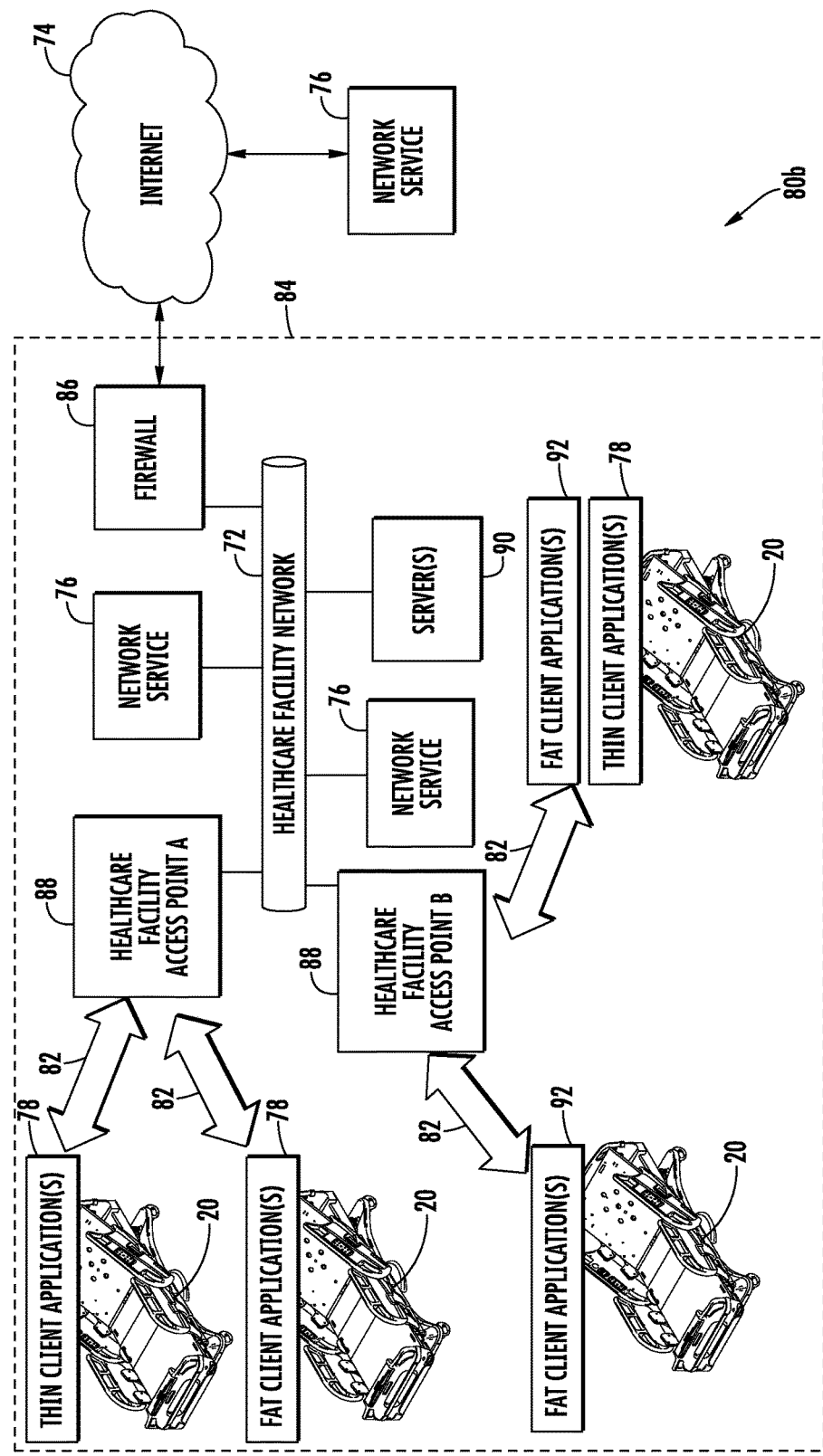
FIG. 5 is yet another diagram of an illustrative layout of a patient support apparatus communication system showing multiple patient support apparatuses running either or both of thin and fat client applications.

FIG. 5 illustrates another example of a patient support apparatus software infrastructure layout 80b that can be implemented with one or more patient support apparatuses 20. In the layout 80b shown in FIG. 5, some patient support apparatuses 20 have thin client applications 78 implemented thereon, while other patient support apparatuses 20 have both thin client applications 78 and one or more fat client applications 92. Still further, at least one patient support apparatus 20 has only a fat client application 92 operating thereon. Fat client applications 92 may be adapted to perform any of the potential functions described above that can be performed by thin client applications 78 (e.g. patient assessment applications, sensors monitoring and/or data collection algorithms, maintenance monitoring/scheduling applications, billing applications, patient care protocol management application). The only difference between thin client applications 78 and fat client applications 92 is that fat client applications 92 rely more heavily on the local controller 52 for carrying out their functions, and less on the network service 76 than do thin client applications 78. That is, while fat client applications 92 still rely on at least periodic access to network service 76 to perform their full functionality, fat client applications 92 are able to perform more functions in the absence of the connection to the network service 76 than a thin client application 78.

Figure 6:
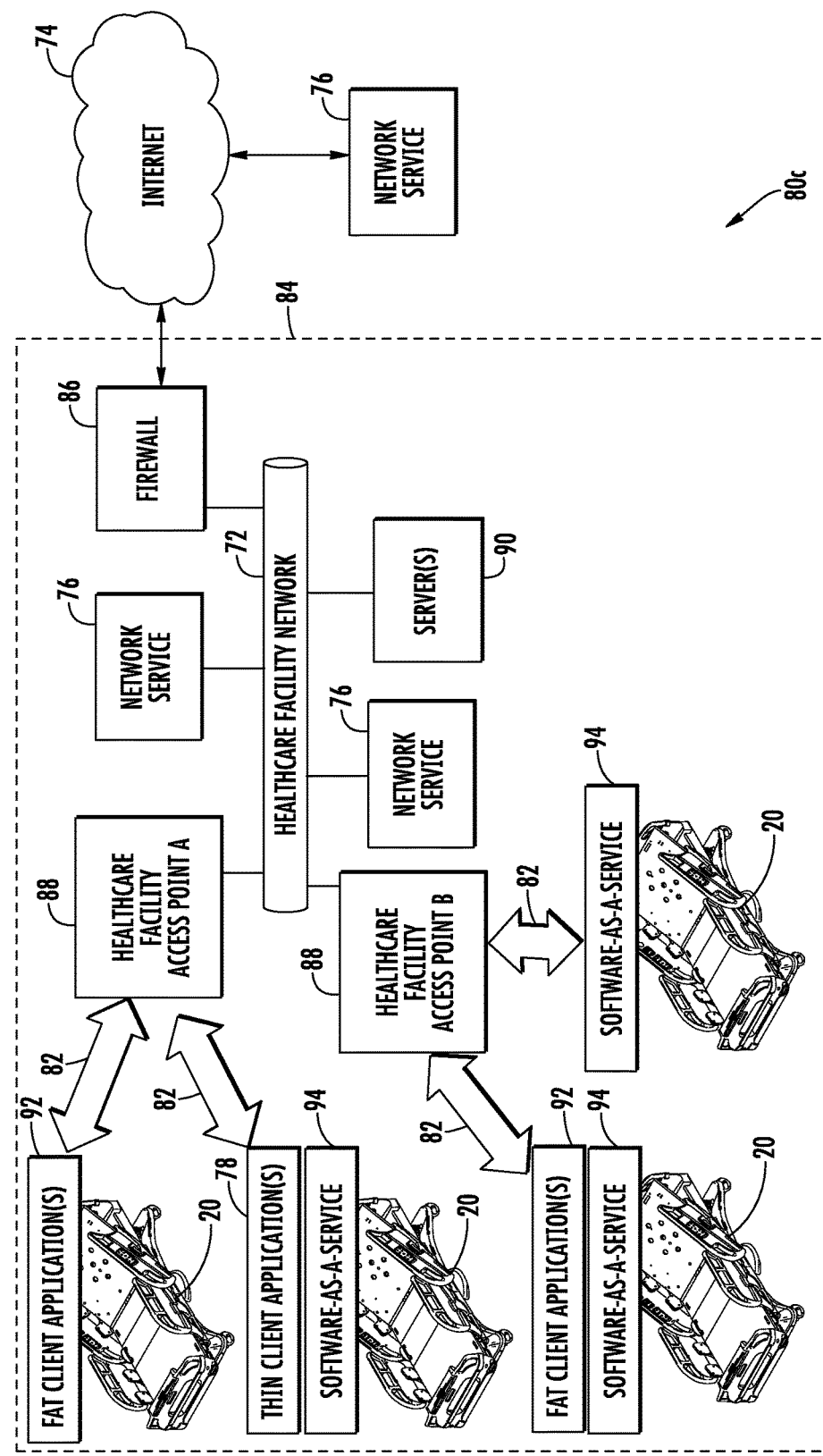
FIG. 6 is still another diagram of an illustrative layout of a patient support apparatus communication system showing multiple patient support apparatuses running any one or more of thin client, fat client, and Software-as-a-Service applications.

FIG. 6 illustrates yet another example of a patient support apparatus software infrastructure layout 80c that can be implemented with one or more patient support apparatuses 20. As with layouts 80, 80a, and 80b, those components that are the same as those found in layouts 80, 80a, or 80b are labeled with the same reference number and operate in the same manner as has been previously described. Those components that are not found in layouts 80, 80a, or 80b are identified with a new reference number.

Layout 80c differs from layouts 80, 80a, and 80b in that at least one patient support apparatus 20 is included within the healthcare facility 84 that is operating a Software-as-a-Service application 94. The Software-as-a-Service (SaaS) applications 94 differ from the thin client applications 78 and the fat client applications 92 in that the network service 76 which interacts with the SaaS application 94 is hosted by an entity other than the healthcare facility. That is, although the SaaS application 94 may utilize a thin or fat client architecture to carry out its functions, the network service 76 will typically be hosted by a company that is not the hospital, or healthcare institution, that owns or operates facility 84. In many cases, although not all cases, the SaaS application will therefore interact with a network service 76 that is located on the service side of the firewall 86. In some embodiments, the network service 76 that interacts with the SaaS application 94 is hosted by the company that manufacturers patient support apparatus 20, or a company that has contracted with the manufacturer of the patient support apparatus 20.

As shown in the example of FIG. 6, some patient support apparatuses 20 are only operating a SaaS application 94, while other patient support apparatuses 20 are operating a SaaS application in addition to other applications, such as a thin client application 78 or a fat client application 92. Still other patient support apparatuses 20 are operating one or more thin or thick client applications 78 or 92 without operating any SaaS applications. The SaaS applications 94 may carry out any of the functions described above that can be performed by the thin or fat client applications (e.g. patient assessment applications, sensors monitoring and/or data collection algorithms, maintenance monitoring/scheduling applications, billing applications, patient care protocol management application).

It will be understood by those skilled in that art that, although FIGS. 4-6 show patient support apparatuses 20 as all being identical to each other, this does not need to be the case. Different types of patient support apparatuses 20 may be used within a given facility 84. For example, as was noted previously, patient support apparatuses 20 include, but are not limited to cots, beds, stretchers, recliners, and/or operating tables. Thus, in the layouts of FIGS. 4-6, it is to be understood that references to patient support apparatus 20 are meant to include any of these types of patient support apparatuses, and that a mix of such support apparatuses may be included in any of layouts 80a, 80b, and 80c. Further, it will also be understood that different versions of thin client applications 28 may operate for different types of patient support apparatuses 20. Still further, in some layouts, completely different thin client applications may be available for different types of patient support apparatuses. In other words, an operating table might use a different application 78 than a bed, while a stretcher might use a thin client application 78 that is different from those that operate on a bed. Similar variations are possible for both fat client applications 92 and SaaS applications 94. Other variations are also possible.

Figure 7:
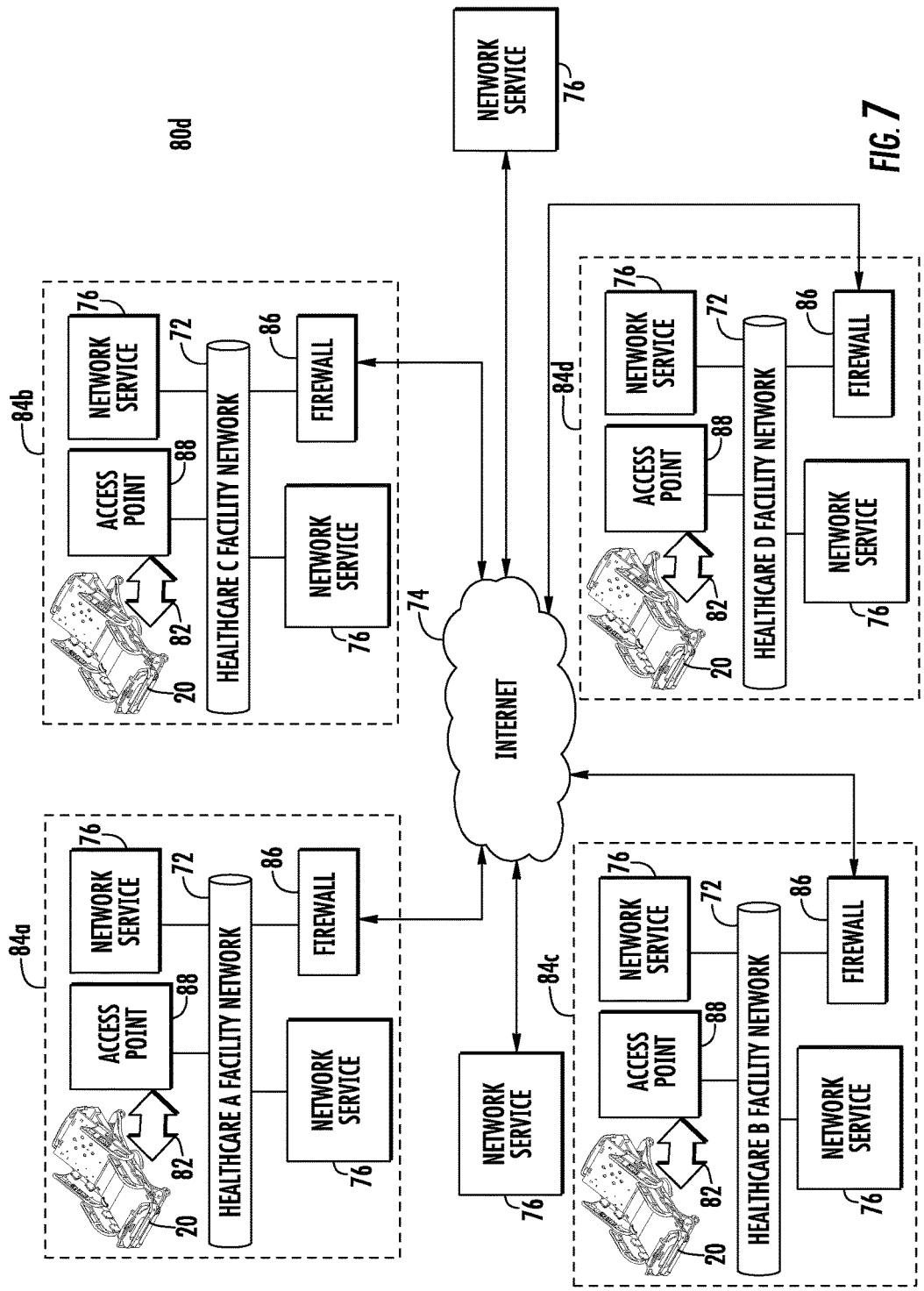
FIG. 7 is another diagram of an illustrative layout of a patient support apparatus communication system that includes multiple healthcare facilities.

FIG. 7 illustrates yet another patient support software infrastructure layout 80d that can be implemented with one or more patient support apparatuses 20. As with layouts 80, 80a, 80b, and 80c, those components in layout 80d that are the same as those found in the previously described layouts are labeled with the same reference number and operate in the same manner as has been previously described. Those components that are not found in layouts 80, 80a, 80b, or 80c are identified with a new reference number.

FIG. 7 differs from the previously described layouts 80 in that it includes multiple healthcare facilities 84 (84a, 84b, 84c, and 84d). FIG. 7 also differs from the previously described layouts 80 in that specific type of software applications (e.g. thin client, fat client, and/or SaaS) implemented on the various patient support apparatuses 20 are not identified. This lack of identification is intended to show that any of these three types of software applications may be implemented on any of these patient support apparatus, including any combinations and/or permutations of these types of software. Further, not only can the software applications on one or more patient support apparatuses 20 within a given healthcare facility 84 vary between the patient support apparatuses 20 within that facility, they can also vary from facility to facility.

Although the software infrastructure layout 80d of FIG. 7 only shows four healthcare facilities connected to the network service 76 that is accessible via the Internet 74, it will be understood that this is only an arbitrary example provided for purposes of illustration. Further, while each facility 84 only shows a single patient support apparatus 20 and a single access point 88, this number will vary from facility 84 to 84. Still further, although FIG. 7 shows each healthcare facility having two local network services 76, this number can also vary in different facilities 84. Finally, although FIG. 7 illustrates each healthcare facility 84 as lacking any servers 90, it will be understood that this omission is merely for purposes of space saving convenience, and that healthcare facilities 84 will typically include one or more servers 90 on their local networks 72.

Infrastructure layout 80d is especially useful for software applications (thin, fat, or SaaS) that gather data from patient support apparatuses 20 across multiple healthcare institutions and use the data for billing purposes (e.g. patient support apparatus 20 usage data), for carrying out population studies, for evaluating compliance with patient care protocols that have patient support apparatus-related components, for ensuring that the patient support apparatuses 20 are properly maintained, and for other purposes, a number of which will be discussed in greater detail below. This list of potential uses, however, is not meant to suggest that these types of applications cannot also, or alternatively, be carried out using a local network service 76 (i.e. one on the network 72 inside the respective firewall 86).

Figure 8:
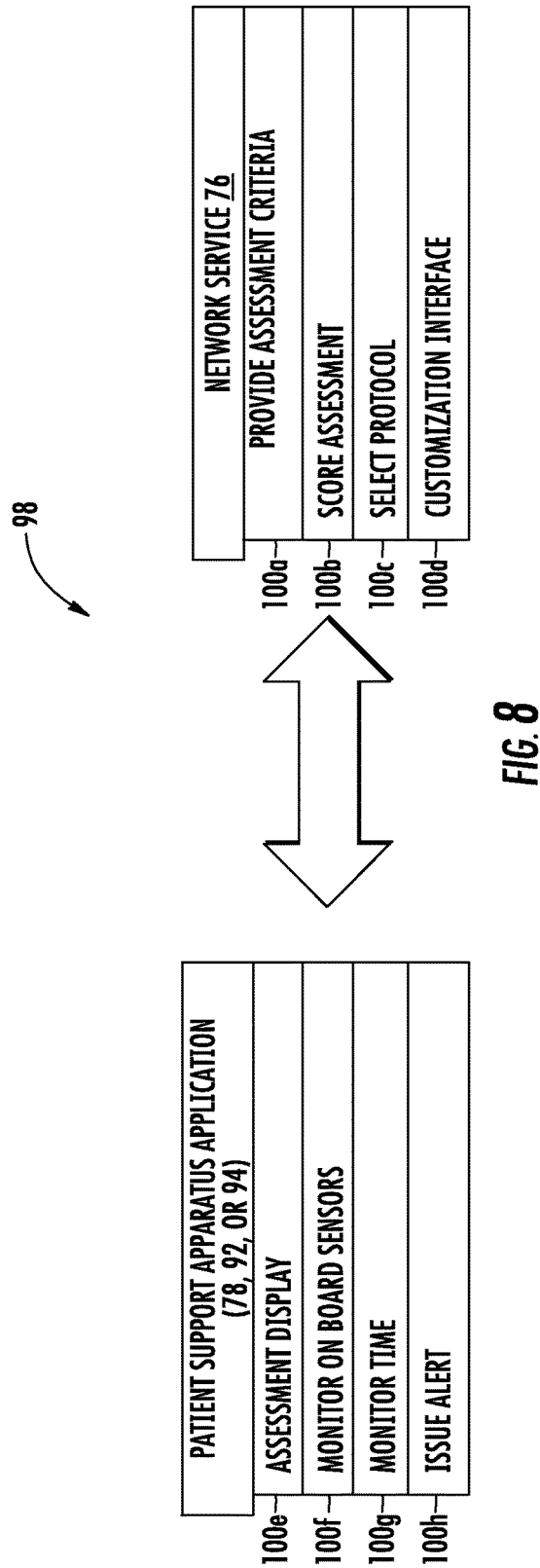
FIG. 8 is a diagram of an illustrative architecture of an assessment software application that may be used with any of the communication systems and patient support apparatuses described herein.

FIG. 8 illustrates one potential arrangement of a patient assessment software application 98 that operates both on patient support apparatus 20 and network service 76. The application 98 shown in FIG. 8 can be a thin client application 78, a fat client application 92, or a SaaS application 94. It will be understood that the particular arrangement shown in FIG. 8 is merely an illustrative example of the types of applications that may operate on patient support apparatus 20 and interact with one or more network services 76, and that modifications to the arrangement shown therein can be made such that some functions carried out by the patient support apparatus 20 are carried out by the network service 76, and vice versa. Further, it will be understood that, although application 98 relates to software used in assessing an aspect of a patient's health, the principles discussed below in regard to this application 98 can be applied to any of the other types of applications discussed herein.

The patient assessment software application 98 of FIG. 8 is specifically designed for assessing a patient's risk of developing bed sores and implementing a patient care protocol based on that assessment. The application 98 includes a plurality of features or functions 100. FIG. 8 illustrates where portions of the software that carry out each of these functions or features 100 reside, or more specifically, where the computations necessary for carrying out each of these functions or features 100 take place. As shown, patient assessment application 98 includes four features or functions 100a, 100b, 100c, and 100d that are computationally performed by the network service 76, and another four features 100e, 100f, 100g, and 100h that are computationally performed by controller 52 on patient support apparatus 20. The results of these computations are shared between controller 52 and network service 76, as needed, using communication link 82.

Patient assessment software application 98 includes an assessment display function 100e that is performed by controller 52 at patient support apparatus 20. Display function 100e carries out the display of any and all information that is necessary for performing the functions of assessment application 98. In the patient support apparatus 20 shown in FIG. 2, controller 52 carries out the display function 100e by controlling the information displayed on display 66, which is located in the footboard 32 of patient support apparatus 20. More specifically, controller 52 carries out display function 100e by controlling the display of any icons, menus, graphics, or other user interface items on display 66 that are used in the patient assessment software application. The content and/or definition of the items displayed by controller 52 on display 66 may be dictated in whole or in part by network service 76, as will be discussed below.

Assessment criteria function 100a (FIG. 8) of patient assessment application 98 is carried out by network service 76. The assessment criteria function 100a refers to the selection and/or definition of what criteria are going to be used in the patient assessment. As one example, the assessment criteria function may refer to using the Braden scale for assessing a patient's risk of developing bed sores. If this is the criteria, then the corresponding network service 76 stores the questions and contents of the Braden scale assessment. If a different method for assessing the bed sore risk is used—such as a modified Braden scale assessment, or a completely different assessment—then assessment criteria function 100a stores this modified or different assessment. In many instances, the assessment will include, but not necessarily be limited to, a list of questions that a caregiver is required to answer about a patient. With respect to the Braden scale, these questions relate to the patient's sensory perception, skin moisture, patient activity, patient mobility, nutrition, and friction and shear. Such question may differ if a different assessment is used. However, whatever assessment is used, the definition and contents of that assessment are stored at network service 76.

When a caregiver begins the assessment application 98, controller 52 may already have a local copy of the assessment criteria function 100a stored at network service 76 by way of a previous communication with network service 76 via link 82. However, in at least one embodiment, application 98 is configured, upon startup, to contact network service 76, if it is currently available, and either to download the latest version of the assessment criteria function 100a, or to confirm that the controller 52 at the patient support apparatus has the latest assessment criteria function 100a stored locally in memory 54. If network service 76 is unavailable at the time of startup of application 98, then controller 52 will, in some embodiments, issue an alert on display 66 indicating that the network service 76 is currently unavailable, and ask the caregiver if he or she would like to continue using the local copy of the assessment criteria function 100a. Regardless of whether the caregiver selects to continue or not, application 98 will continue to make attempts at contacting network service 76 until communication is established, at which point controller 52 will indicate this successful communication on display 66.

Network service 76 also stores the data which defines how an assessment is scored at feature 100b. That is, while function 100a defines the questions and criteria that are used to assess the patient, function 100b defines the manner in which the answers to the questions of function 100a are converted into a numeric score, or, in some cases, a qualitative score. For example, the Braden scale customarily converts the various assessment questions into a score that ranges from 6 to 23, where a score of 23 represents the lowest risk of developing bed sores, while a score of 6 represents the highest score of developing bed sores. Scoring feature 100b therefore contains the intelligence necessary for performing this scoring, or a modified version of this scoring, which a hospital administrator can implement using the customization interface 100d, as will be discussed in greater detail below.

The protocol selection feature 100c is also stored on network service 76 and determines the patient care protocol that should be followed in light of the score that resulted from the analysis carried out by feature 100b. In other words, feature 100c, using the example of the Braden scale again, determines what patient care protocol should be followed for each of the seventeen different numeric Braden scale scores. In many instances, the intelligence of the protocol selection feature 100c will group the scores into ranges, and any scores in a particular range will result in the same patient care protocol being recommended, while scores in a different range will result in either a different patient care protocol, or no patient care protocol.

As an illustrative example, if a particular patient scores a 10 on the Braden scale, the data stored at network service 76 for feature 100c will be used by network service 76 to select a particular patient care protocol that helps to reduce the likelihood of a patient developing bed sores. The definition of the patient care protocol can vary, but in one embodiment includes—among potentially other features—a definition of how often a patient should be turned. In some instances, a higher risk of bed sores for a particular patient will generally correspond to a higher frequency of patient turns, although not all assessment programs 98 need to be implemented in this manner. In other embodiments, the patient care protocol may specify certain characteristics or settings of the mattress 36 supported on patient support apparatus 20. For example, the protocol might specify that a low air loss feature on the mattress be turned on in order to help reduce moisture build up, which is correlated with increased likelihood of bed sores. The patient care protocol might also specify an inflation pressure for one or more of the inflatable bladders inside of the mattress. In still other embodiments, the patient care protocol might specify one or more mattresses, or types of mattresses, that need to be used with this particular patient (and if they are not present on the patient support apparatus 20, a caregiver will be required by the protocol to change the mattress to match the protocol). Still other aspects and definitions of the patient care protocol may also be contained within the protocol select feature 100c.

After a particular patient care protocol has been selected using the selection feature 100c, patient support apparatus 20 is ready to implement those portions of the patient care protocol that relate to patient support apparatus 20, or mattress 36, or any other feature or device that is in communication with patient support apparatus 20. In some embodiments, the patient care protocol selected by feature 100c will require the monitoring of one or more sensors on board patient support apparatus 20, such as, but not limited to, force sensors 62. This is performed locally by controller 52 and carried out as part of function 100f. Further, in some patient care protocols, the passage of time needs to be measured, such as, for example, the time since a patient was last turned. This monitoring of time is also carried out locally in application 98 via function 100g. Application 98 also includes an alerting feature that is carried out whenever application 98 determines that the patient care protocol isn't being followed, or the protocol requires some action by the caregiver. For example, if the patient care protocol requires that a patient be turned every two hours, application 98 will issue an alert after the passage of two hours without the patient being turned. The alert can be a local alert, a remote alert, or both. If local, it can involve a message displayed on display 66, or an aural sound, or the illumination or flashing of one or more lights. If remote, controller 52 forwards the alert via transceiver 60 to the appropriate destination on network 72 for transmitting the alert to the desired caregivers (e.g. to a remote alerting server 90 discussed above).

As another example, an alert may be issued by application 98 if the patient care protocol specifies that a specific mattress be used with patient support apparatus 20 and controller 52 does not detect the appropriate mattress type (via interface 58), or if the patient care protocol specifies that a low air loss feature of the mattress 36 be turned on, and this is not turned on (as controller 52 would detect via interface 58). In general, any parameters of the patient care protocol that controller 52 is capable of confirming or analyzing will generate an alert if the confirmation is negative, or if the analysis leads to a result calling for caregiver attention.

While it was briefly mentioned above, it bears repeating that the particular division of functions 100 of application 98 shown in FIG. 8 can be varied. That is, in some embodiments of assessment application 98, any of functions 100f, 100g, and/or 100h might also be performed via network service 76. Indeed, in some embodiments, even the control of the screen space of display 66 of feature 100e could be carried out by way of network service 76. Alternatively, any one or more of the features or functions 100a, 100b, 100c, and/or 100d could be carried out locally by controller 52 on patient support apparatus 20. In some embodiments, controller 52 will retain in memory 54 a local copy of all of the data and instructions associated with the features or functions 100a, b, c, and d that are carried out by assessment application 98 and utilize that local copy if communications link 82 is broken, or if controller 52 is otherwise unable to communicate with service 76. However, when service 76 is available, application 98 will use the network service 76 to perform, rather than the local copy. In still other embodiments, controller 52 may not have a local copy of any of the features 100 of network service 76, in which case, if the service is temporarily unavailable, then the application 98 will not operate correctly.

While not required for assessment application 98 to operate properly, the particular embodiment of assessment application 98 shown in FIG. 8 also includes a customization interface 100d that is configured to operate via network service 76. Customization interface 100d is adapted to allow authorized personnel at the particular healthcare institution to change any of the data or instructions associated with any of the network features or functions 100a, 100b, and/or 100c. This allows a healthcare facility to easily implement their own custom patient care protocols, their own criteria for determining when such protocols are to be used, and/or their own criteria for interpreting the results of their custom assessments. In other words, customization interface 100d allows authorized personnel to change what bed sore assessment will be used by network service 76 (e.g. a healthcare institution could change from using the Braden scale to another criteria). It also allows authorized personnel to change how the results of the assessment questions are scored (feature 100b). Still further, it allows authorized personnel to change which protocols correspond to which scores, and how those protocols are defined (feature 100c).

Customization interface 100d therefore provides users with greater flexibility for carrying out patient care in a manner that reflects the judgment and opinions of the particular healthcare institution that is running application 98. This flexibility is not present in prior art patient support apparatuses where, when they include features regarding patient care protocols, they are hard coded into the patient support apparatus itself and cannot be easily changed. Further, this flexibility allows a healthcare institution at least several advantages over prior art patient support apparatuses.

First, this flexibility allows a healthcare institution to easily change their patient care protocols as medical research and health information is developed and discovered. For example, if a new medical study is published indicating that reducing bed sores for patient's having a Braden scale score of 10 requires a patient to remain immobile for no longer than X minutes, then the healthcare institution can update their patient care protocol to require patient turns every X minutes, or some other time period based upon the published research. Alternatively, if medical research shows that the Braden scale is not as accurate as another measurement of bed sore risk, then the medical institution can switch function 100a to include the questions, data, and other information for that different measurement.

Second, this flexibility allows a healthcare institution to more easily monitor the effectiveness of its patient care protocols. For example, an evaluation feature can be added to application 98, or another separate application can be implemented, that records the actual steps taken by the caregiver, including when patient turns are implemented, how much time passes between turn intervals, what mattresses are used, what mattress setting were used with a patient, etc. This information is gathered for all patient support apparatuses 20 within the healthcare institution and stored in a central location. Further, this information can then be easily compared to an EMR database, or other database, that contains the actual history of bed sore developments for patients in that healthcare facility. By appropriately correlating the sensor data gathered from the patient support apparatuses 20 with the clinical records of the patients that have been supported thereon, the effectiveness of the patient care protocol can be evaluated. In other words, if it turns out that patients with a particular bed sore risk score are still developing bed sores with a patient care protocol X, then the healthcare facility can easily use customization interface 100d to change the patient care protocol corresponding to that bed sore risk score. Other modifications can also be made, depending upon the outcome of the correlation analysis.

As was noted above, in some embodiments of assessment application 98, application 98 carries out the monitoring function 100g by monitoring the outputs of one or more sensors, such as, but not limited to, force sensors 62. It will be understood that the precise nature of the monitoring, as well as the sensors monitored, will vary from application to application. In one embodiment, assessment application 98 continuously, or nearly continuously, monitors the outputs of force sensors 62 and keeps track of the amount of movement of the patient supported on patient support surface 28. Further, controller 52 carries out function 100g by monitoring the outputs of forces sensors 62, and/or other sensors, to determine when a patient has turned, whether on his or her own, or with the help of a caregiver. Controller 52 may also monitor still other sensors on board patient support apparatus 20, such as, but not limited to, one or more vital sign sensors, a patient pressure interface mat positioned on top of—or integrated into—the mattress, or still other sensors. The manners in which these sensors can be monitored for determining such things as patient turning, patient movement levels, vital signs, and other information can be accomplished in a variety of different manners, some of which are disclosed in commonly assigned U.S. patent application Ser. No. 61/791,117, filed Mar. 15, 2013, by Michael Hayes et al. and entitled PATIENT SUPPORT APPARATUS WITH PATIENT INFORMATION SENSORS, the complete disclosure of which is hereby incorporated by reference herein.

In addition to, or in lieu of patient assessment application 98, a variety of different applications can operate as a thin client application 78, or a fat client application 92, or a SaaS application 94 on patient support apparatus 20. While the following list and description of some examples of such applications are provided, this list is not meant to be exhaustive, and other applications and/or modifications to these applications can be made.

Another patient assessment application that can operate on patient support apparatus 20 (as a thin client, fat client, or SaaS application), is a fall risk patient assessment application. Such a fall risk assessment application operates similar to the bed sore assessment application 98 except it is modified to address the potential of a patient falling, rather than the potential of a patient developing bed sores. Such an application includes one or more features that are comparable to bed sore assessment application 98, such as: (1) a list of criteria or questions to be answered in a manner similar to function 100a of application 98; (2) an algorithm or other intelligence for scoring the results of the questions, similar to feature 100b of application 98; (3) a selection and definition of a fall prevention patient care protocol that will be used in response to the assessed score (similar to feature 100c of application 98); (4) and a plurality of features that monitor sensors and/or time, and that issue necessary alerts (similar to features 100f, 100g, and 100h of application 98). Such fall prevention protocols will typically include one or more of the following requirements: the brake on the patient support apparatus is set; the height of the frame 26 is at its lowest height, or at least less than a threshold height; the side rails 62 are positioned in an up position, and a patient exit alert system is activated. The protocol also specifies, in some embodiments, a specific setting for the patient exit alert system (for those patient support apparatuses that have different thresholds for triggering the patient exit alert).

Another application that can operate on patient support apparatus 20 as a thin client, fat client, or SaaS application is a ventilator patient care protocol application. Such a ventilator patient care protocol specifies what steps a caregiver is supposed to take with respect to patient support apparatus 20 (and/or mattress 36) when a patient using the patient support apparatus 20 is connected to, or about to be connected to, a ventilator. While the specific patient care protocol can vary, one protocol will customarily require that the angle of the Fowler section of the patient's bed be maintained above a certain threshold angle, such as thirty degrees. By keeping the patient's torso in an upright position, the likelihood of ventilator associated pneumonia (VAP) is reduced. The ventilator application therefore instructs the caregiver to configure the patient support apparatus in such an upright position and, if the patient support apparatus is so equipped, activate a lockout feature that prevents the patient support apparatus from being moved to an angular position less than the threshold. In some embodiments, the ventilator application can prescribe an angular orientation of the Fowler portion of the bed that can be customized for a particular healthcare institution via a customization interface (similar to customization interface 100d of application 98). In still other embodiments, the ventilator application can be configured to run automatically when the patient support apparatus detects the presence of a nearby ventilator via near field communication. Such detection can be carried out in any of the manner disclosed in the commonly assigned U.S. patent application Ser. No. 13/802,992, filed Mar. 14, 2013 by applicants Michael Hayes et al, and entitled COMMUNICATION SYSTEMS FOR PATIENT SUPPORT APPARATUSES, the complete disclosure of which has already been incorporated herein by reference.

The ventilator protocol application may also include a customization interface, similar to customization interface feature 100d of application 98. This customization interface allows the ventilator protocol to be modified in accordance by authorized healthcare administrators. Such customization allows the administrator to sets the minimum threshold angle of the Fowler section of the patient support apparatus which is not to be broken during the implementation of the ventilator protocol. Other customizations are also possible.

Another application that can operate on patient support apparatus 20 as a thin client, fat client, or SaaS application is a compliance monitoring application similar to that described above. Such a compliance monitoring application monitors how well any of the various patient care protocols (including, but not limited to, the bed sore prevention and fall prevention protocols mentioned above) are followed. Such a compliance application monitors and records the outputs from all of the sensors on the patient support apparatus that output information that can be used to determine whether any aspect of the patient care protocol has been followed or not. As an example, if a fall prevention protocol is implemented that requires the side rails 62 on the patient support apparatus 20 to be maintained in an up position, sensors (not shown) on patient support apparatus 20 will forward their outputs to controller 52 which will record these and forward them onto the network service 76. The time at which a side rail goes out of compliance is recorded, as well as the total duration of time that the side rail is out of compliance. Network service 76 makes this information available to the healthcare institution so that administrators can gauge how effectively their protocols are being followed.

As another example, a compliance application can be used to monitor compliance with patient care protocols used for preventing ventilator associated pneumonia (VAP). As discussed, such protocols typically require that the Fowler portion of a bed (e.g. head section 38 of patient support apparatus 20) be maintained at an angle above thirty degrees, or some other threshold. Controller 52 communicates with a sensor (not shown) that measures the angle of the Fowler portion on patient support apparatus 20 and—when carrying out the compliance application—records the outputs from this sensor and forwards them to the compliance network service.

One or more billing applications can operate on patient support apparatus 20 (as thin client, fat client, or SaaS applications) that record the amount of time a patient is in patient support apparatus 20, as well as the amount of usage of certain features on the patient support apparatus 20 which are used with a particular patient. This information is forwarded by the application to the corresponding network service 76 where it is made available to the healthcare administrators who can use it to bill patients based on the amount of time and/or usage of patient support apparatus 20, and/or any of the individual features of patient support apparatus 20.

One or more maintenance applications can also, or alternatively, operate on patient support apparatus 20 as thin client, fat client, and/or SaaS applications. In one embodiment, a maintenance application operates on patient support apparatus 20 that counts the number of times each of the various actuators 68 on board patient support apparatus 20 are used. These actuators include the tilt actuator 68a, deck actuator(s) 68b, lift actuator(s) 68c, and/or brake actuator(s) 68d. The maintenance application records the counts for each of the individual actuators and compares these counts to thresholds corresponding to each of these various actuators. If any of the counts exceed the corresponding threshold, a maintenance alert is issued (either locally, remotely, or both) by the maintenance application. Preventative maintenance can then be performed on the patient support apparatus based upon the device's actual usage, rather than a simple passage of time (which may or may not reflect use conditions). The maintenance application therefore helps ensure that patient support apparatuses 20 receive the proper care in a timely manner.

In addition to counting the physical movement of various components of patient support apparatus 20, the maintenance application can also keep track of the number of times one or more rechargeable batteries on the patient support apparatus 20 are charged and discharged. Further, the extent of the discharging and recharging can be monitored and recorded. This information is then transmitted to network service 76 which uses the information to determine when the rechargeable batteries should be replaced. This helps ensure that the rechargeable batteries are replaced on a timely basis, but not unnecessarily often.

The maintenance application can also, in some embodiments, gather and store the usage data for comparison with a database containing actual failures or component breakdowns. In such embodiments, the data gathered from the maintenance application is compared to the database of component failures and modifications to the maintenance schedule can be adjusted, if necessary, based on the results of the comparison. Still further, mean times between failures (MTBF) of components in actual field use can be calculated, and this information can be used to set schedules and/or thresholds for preventive replacements of components prior to their breaking down so as to minimize down time.

Another type of application that can also, or alternatively, operate on patient support apparatus 20 as a thin client, fat client, and/or SaaS application is a data-gathering and analysis application. The data gathering refers to the gathering of any and/or all sensor information that the patient support apparatus is capable of generating. This information is forwarded by the application to a network service 76 (whether inside firewall 86 or outside firewall 86) that stores the data and allows population studies on large numbers of patient support apparatuses 20 to be performed. The types of studies are customizable according to the interests of the manufacturer of the patient support apparatus 20, or according to the interests of one or more healthcare facilities. Such studies might include, for example, studies that look for correlations between patient movement on support surface 28 (as measured by force sensors 68) and the subsequent exiting of the patient from the patient support apparatus 20. Such studies may be capable of finding patterns between certain movements and the subsequent exiting of a patient from the support surface 28. By finding such patterns, it will be possible to design an exit alert system application that can issue exit alerts a greater amount of time ahead of the patient's exit than existing alert systems. By issuing such alerts further in advance of patient exit, a caregiver is given more time to come to the room the patient is in and assist him or her from exiting from the support apparatus 20, thereby reducing the risk of a patient fall. Other types of studies may also be carried out using such data gathering applications.

Yet another type of application that can also, or alternatively, operate on patient support apparatus 20 as a thin client, fat client, and/or SaaS application is an infection control application. The infection control application monitors what equipment is associated with patient support apparatus 20 and maintains a log of this equipment so that, if a contagious infection is later detected, the equipment associated with that patient can be easily identified and sanitized. The determination of what equipment is associated with a particular patient and/or patient support apparatus 20 can be carried out in any of the manners disclosed in the aforementioned commonly assigned U.S. patent application Ser. No. 13/802,992.

Still another type of application that can be added to patient support apparatus 20 is a video application that makes videos available for display on display 66 of patient support apparatus 20. Such videos may be videos that explain how to operate one or more features of patient support apparatus 20. Alternatively, or in addition, such videos may be videos that explain how to service, troubleshoot, or repair any aspects of patient support apparatus 20. Still further, such videos could include information for caregivers about any of the various patient care protocols mentioned above. The content of such videos, however, would be stored remotely, e.g. at the network service 76, in order to reduce the memory burden on board patient support apparatus 20, as well as to allow the contents of such videos to be more easily changed or updated.

Any of the foregoing applications that can operate on patient support apparatus 20 may also include a customization interface feature similar to feature 100d. Such a customization feature allows healthcare institutions to modify the corresponding application to meet their particular needs. Such customization gives the healthcare facility greater flexibility in billing, maintenance, patient care, data collection, and compliance monitoring.

From the foregoing description, it should be clear that control system 50 of patient support apparatus 20 is configured in a manner that is generally similar to current smart phones which can support one or more apps where the apps carry out functions and/or computations that are not all done locally at the smart phone. Instead, such apps typically interact with network services that are available via a 3G, 4G, or WiFi connection to the Internet, although such interaction is generally invisible to the user of the app. In a similar manner, control system 50 is adapted to support the addition of thin, fat, or SaaS patient support apps (applications 78, 92, and/or 94) that can be added to and removed from patient support apparatus 20 and that interact with remote network services 76, wherein such interaction is generally invisible to the caregiver, or other operator, of the patient support apparatus 20. Further, just as with a smart phone app, some of the algorithms used by these patient support apps are defined by the remote network service and can be varied by the remote network service in a manner that is invisible to the user.

Still further, patient support apparatuses 20 are adapted to be able to have new patient support apps installed without requiring a person to physically connect a memory device containing the new app to the patient support apparatus. Instead, control system 50 is configured to automatically search for available patient support apps and display the available apps on display 66. This enables the appropriate personnel at the healthcare facility to download the desired patient support apps to the patient support apparatus by simply choosing the desired patient support apps. If proper authorization is provided, and/or proper payment arrangements are made, the desired apps are automatically downloaded to control system 50 via communications link 82.

Control system 50 is also adapted to support patient support apps that provide new features on the patient support apparatus 20. For example, some patient support apparatuses 20 may be sold to customers with a patient scale system (e.g. a set of force sensors 62 that are able to determine patient weight), but no patient exit detection system. If the customer later desires to add a patient exit detection systems, the customer can download a patient support app (after establishing proper authorization and making the appropriate payment arrangement) that utilizes the existing scale system to implement a patient exit detection system. For example, the patient exit detection system app can utilize the outputs of the force sensors 62 to calculate the center of gravity of a patient positioned on the patient support surface 28 and issue an alert if the patient's center of gravity moves outside of a selected zone. One manner in which these center of gravity and alerting functions may be carried out is disclosed in commonly assigned U.S. Pat. No. 5,276,432 issued to Travis and entitled PATIENT EXIT DETECTION MECHANISM FOR HOSPITAL BED, the complete disclosure of which is also hereby incorporated herein by reference.

Figure 9:
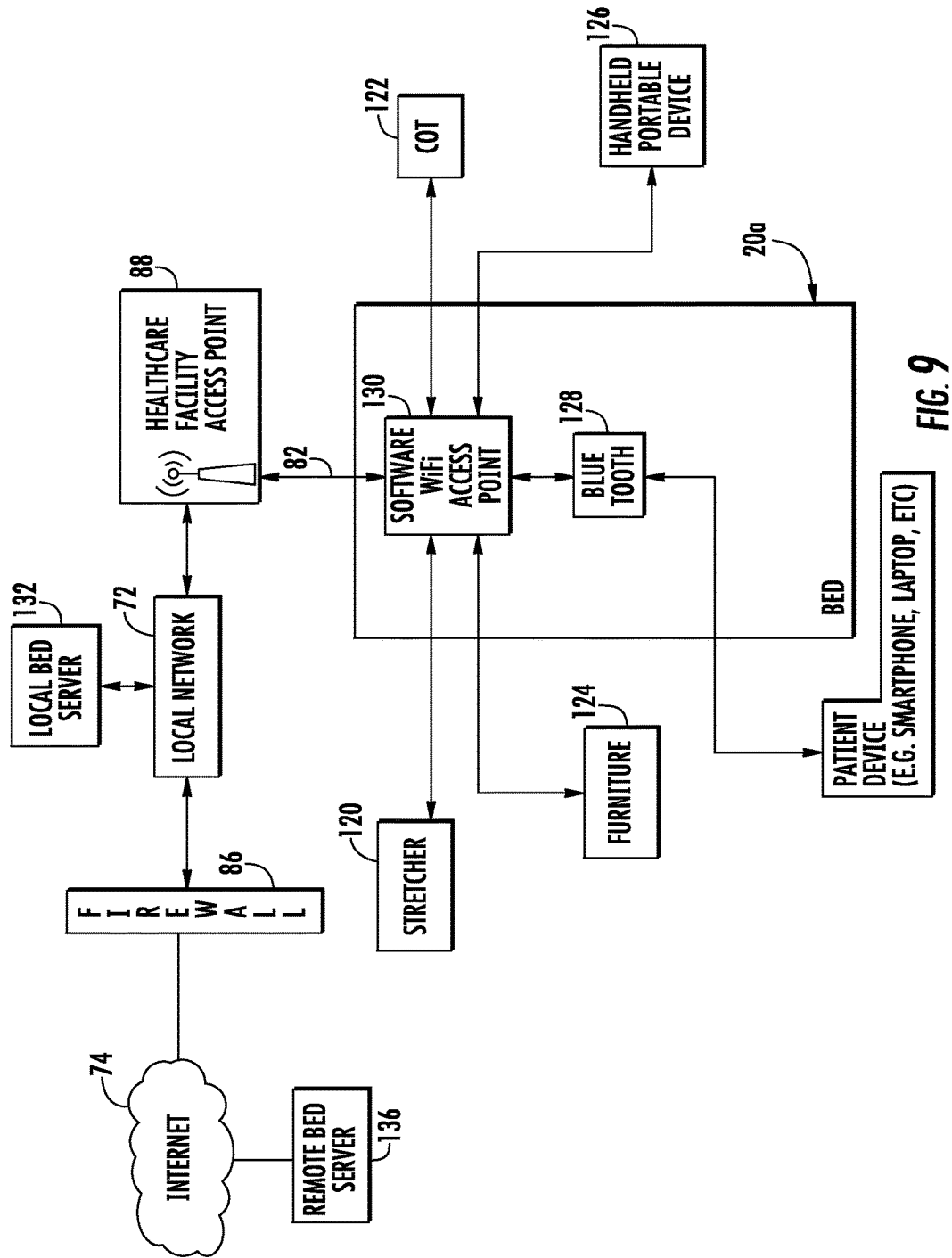
FIG. 9 is a diagram of a patient support apparatus incorporating a wireless hot spot communication feature according to another embodiment of the present invention.
Figure 10:
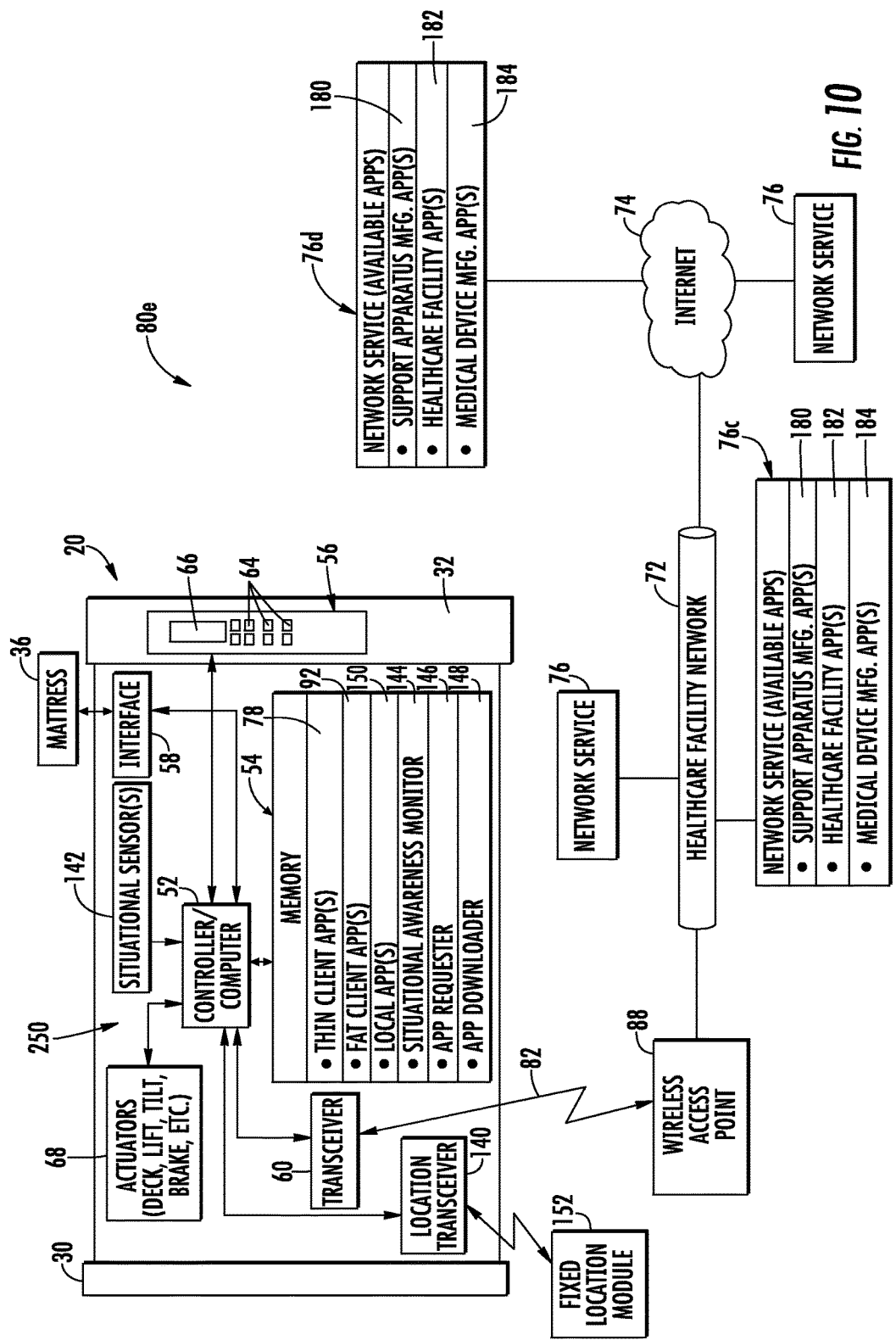
Figure 11:
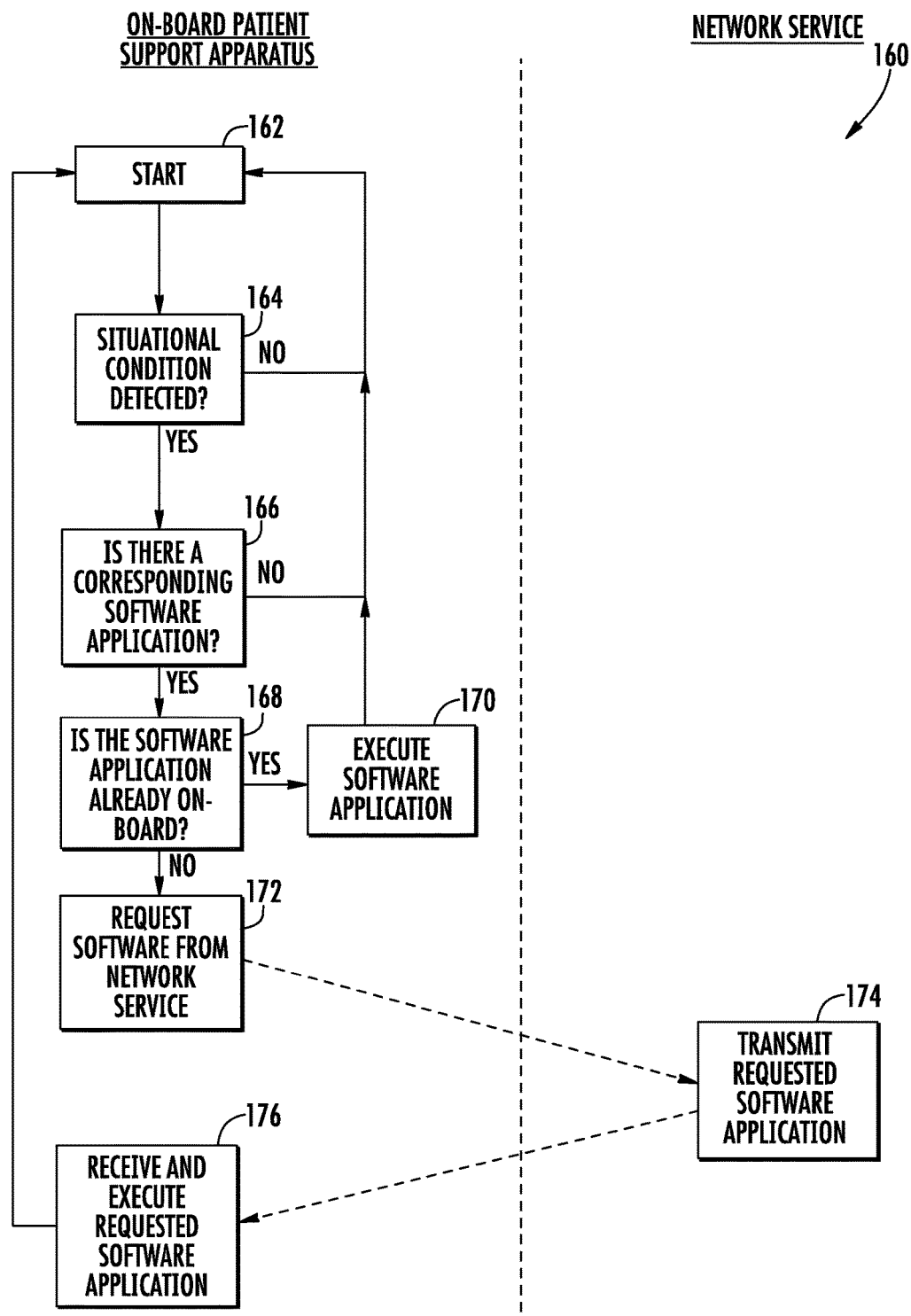
Figure 12:
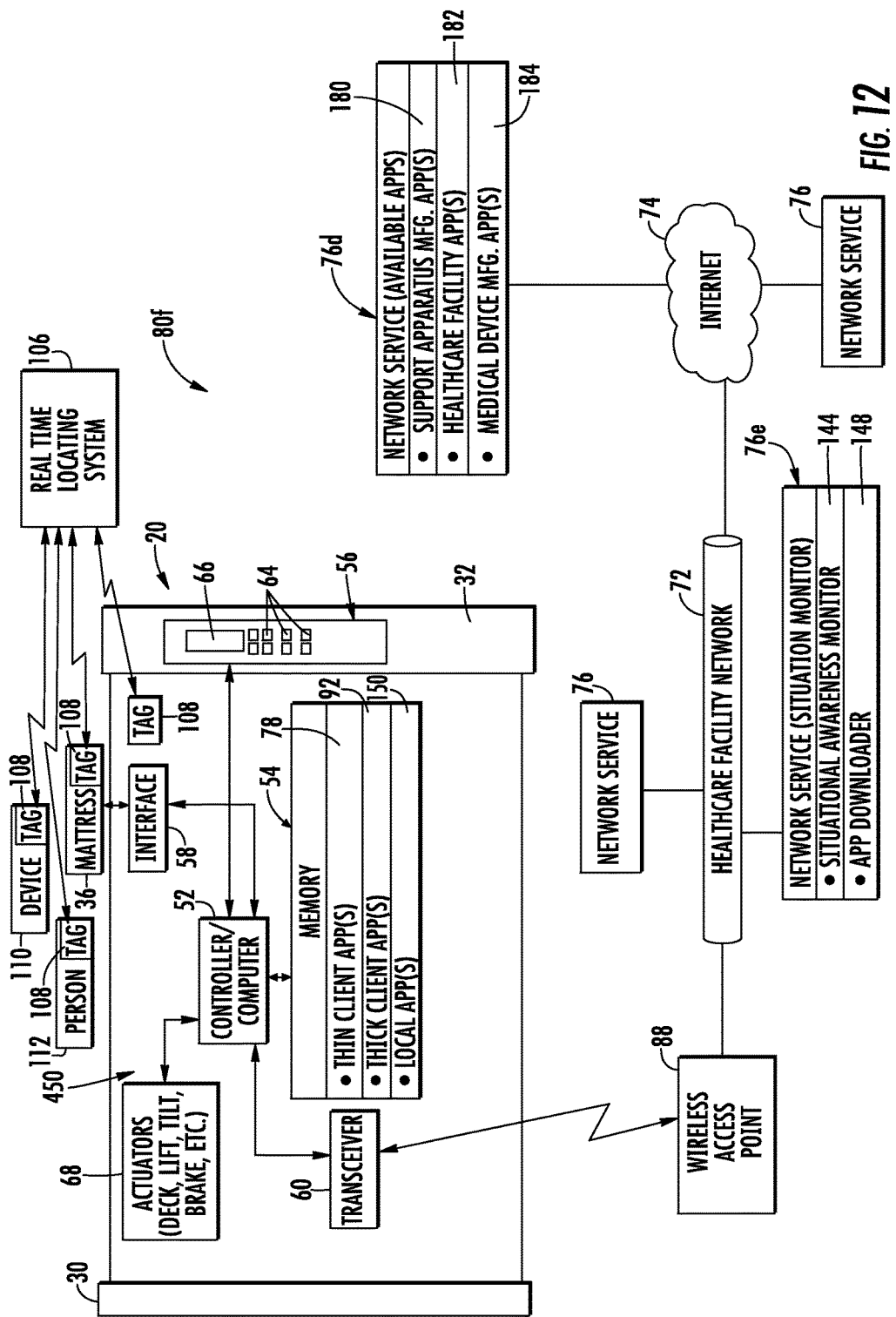
Figure 13:
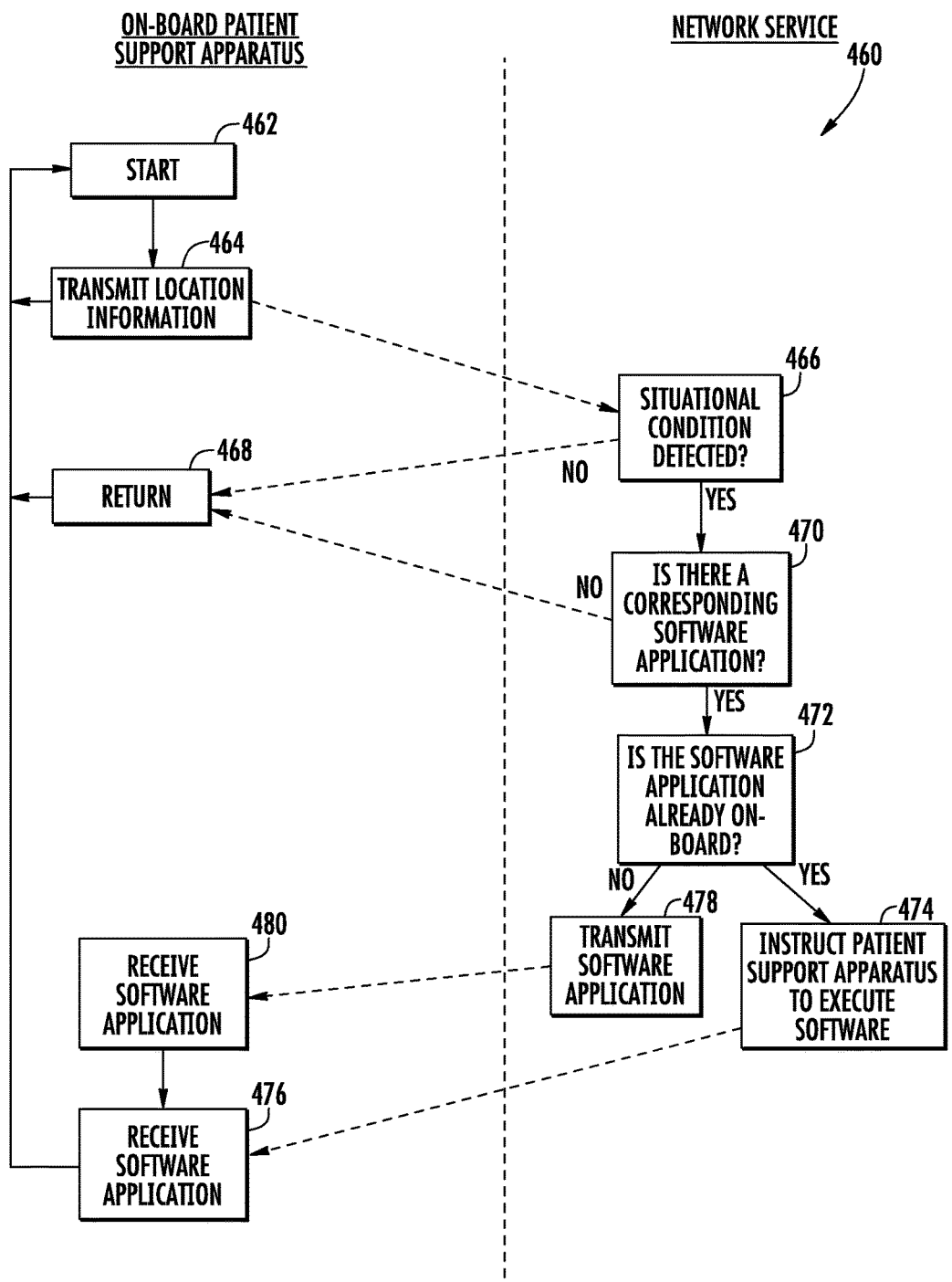

FIG. 9 illustrates another patient support apparatus 20a according to another embodiment of the present invention. Patient support apparatus 20a may or may not include a control system that allows for patient support apps to be downloaded thereto. Indeed, in one embodiment, patient support apparatus 20a includes purely local software that controls the functions of patient support apparatus. In other embodiments, patient support apparatus 20a may have the ability to support thin client, fat client, and/or SaaS applications, as patient support apparatus 20 does. However, regardless of whether the software on patient support apparatus 20a operates only locally, or both locally and remotely, patient support apparatus 20a includes electronic circuitry and programming that create a software wireless access point 130. Software wireless access point 130 is connected by a wireless WiFi connection to any one or more of the wireless access points 88 within the corresponding healthcare facility. Wireless access point 88 is, as noted above, electrically coupled to healthcare communications network 72, and, in some cases, the Internet 74 and any network services 76 that are hosted outside the healthcare facility 84, as well as in the illustrated embodiment, a remote bed server 136.

Software wireless access point 130 provides a mechanism for any of a variety of different devices to communicate with network 72, including any servers that are installed thereon by the healthcare facility, as well as with the Internet 74, and resources or servers in communication with the Internet 74. In the embodiment shown in FIG. 9, a local bed server 132 is shown configured on the local network 72, while a remote bed server 136 is shown configured for Internet communications. In some embodiments, one or both of these servers 132 and/or 136 may be omitted. When included, local bed server 132 functions to receive data transmitted by patient support apparatus 20a (which is a bed in this example, although it will be understood that it could be any other type of patient support apparatus) and make such data available to any other applications or servers running on the healthcare network 72. Local bed server is also configured to communicate and receive data from any other applications or servers (e.g. servers 90, not shown in FIG. 9) running on the healthcare network 72 and to forward such data to one or more patient support apparatuses 20 that are positioned within the healthcare facility. Such information includes, for example, patient information, patient room information, healthcare worker assignment information (e.g. which worker(s) are assigned to which patient(s)), and other information. Remote bed server 136 is capable of performing a variety of different functions, including gathering data from the sensors on board patient support apparatus 20a, and is accessible to patient support apparatus 20a through the Internet.

Software wireless access point 130 allows the patient support apparatus 20a to act as a local WiFi hotspot. Various devices having WiFi capabilities can connect to the access point 130 without having to undergo all of the healthcare facility's security, setup, and initialization procedures. Instead, such procedures, to the extent necessary, can be carried out locally at the patient support apparatus 20a. This enables the user of the wireless access point 130 to tether their device to wireless hotspot 130, enabling them to communicate with network 72 and/or the Internet 74. Further, the manufacturer of the patient support apparatus 20a can configure access point 130 to control the manner in which devices are granted access to access point 130.

Examples of some of the various types of devices that may communicate with a software WiFi access point 130 include, as shown in FIG. 9, a stretcher 120, a cot 122, one or pieces of furniture (such as a recliner) 124, and a handheld portable device 126 (which may be a smart phone, computer tablet, personal digital assistant, portable computer, or other device). Patient support apparatus 20a also includes a second transceiver 128, which in the embodiment shown in FIG. 9, is a Bluetooth transceiver that is in electrical communication with access point 130. Second transceiver 128 enables devices to access access point 130 using protocols different from the protocol of access point 130. As shown, a plurality of one or more patient personal devices 132 (e.g. smart phone, laptops, PDAs, etc.) may connect to WiFi access point 130 using their Bluetooth connection, instead of their WiFi connection. Alternatively, such devices can connect to access point 130 using a WiFi connection (if available).

Various alterations and changes can be made to the above-described embodiments without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

What is claimed is:

1. A patient support apparatus comprising:
a frame;
a support surface supported on the frame;
a display;
a transceiver adapted to communicate with a remote network; and
a computer supported on the patient support apparatus and in communication with the transceiver and the display, the computer adapted to execute an application that is partially carried out on the computer, and that is also partially carried out on a remote network service available on the remote network, wherein the application is adapted to process outputs from a plurality of load cells integrated into the patient support apparatus and adapted to detect an amount of force exerted onto a deck of the patient support apparatus.

2. The patient support apparatus of claim 1 wherein the computer is adapted to execute an additional application that provides a list of questions for assessing at least one of the following: a patient's susceptibility to developing bed sores and a patient's fall risk.

3. The patient support apparatus of claim 2 wherein the remote network service is configurable by employees of a healthcare facility in which the patient support apparatus is positioned such that the employees are able to change the list of questions provided by the application.

4. The patient support apparatus of claim 1 wherein the computer is further adapted to send data from the load cells to the remote network service and to receive processed information back from the remote network service indicating whether a patient has or has not turned while positioned on the patient support apparatus.

5. The patient support apparatus of claim 1 wherein the display is incorporated into the patient support apparatus and the remote network service determines at least one item of information to be shown on the display.

6. The patient support apparatus of claim 1 wherein the computer is further adapted to act as a wireless software access point for the remote network for a device positioned within communication range of the computer, whereby the device communicates with the remote network through the computer.

7. The patient support apparatus of claim 6 further including a second transceiver different from the transceiver, the computer being further adapted to communicate with the device using the second transceiver.

8. The patient support apparatus of claim 6 wherein the device is one of a smart phone and a portable personal computing devices.

9. The patient support apparatus of claim 6 wherein the computer is adapted to provide Internet access to the device.

10. The patient support apparatus of claim 1 further including:
- an elevation adjustment mechanism adapted to raise and lower the frame;
- at least one motor adapted to pivot a section of the support surface about a generally horizontal axis;
- a plurality of side rails coupled to the frame;
- a control panel having controls for controlling the elevation adjustment mechanism and the motor;
- a plurality of wheels; and
- a brake for selectively locking and unlocking the wheels.

11. The patient support apparatus of claim 1 wherein the remote network service is configurable by employees of a healthcare facility in which the patient support apparatus is positioned such that the employees are able to configure what information is provided to the patient support apparatus by the remote network service.

12. The patient support apparatus of claim 11 wherein the remote network service provides a list of questions for assessing an aspect of a patient supported on the patient support apparatus.

13. The patient support apparatus of claim 12 wherein the list of questions provides an assessment of at least one of the following: a patient's susceptibility to developing bed sores and a patient's fall risk.

14. The patient support apparatus of claim 12 wherein the computer receives the list of questions from the remote network service and displays the list of questions on the display.

15. The patient support apparatus of claim 1 wherein the computer is adapted to act as a thin client for a plurality of other remote network services, and to allow a user to choose from the plurality of other remote network services.

16. The patient support apparatus of claim 1 wherein the computer includes a software platform for supporting at least one software-as-a-service (SaaS) application, the SaaS application provided by one of the other remote network services.

17. The patient support apparatus of claim 1 wherein the application monitors compliance with a protocol for providing care to a patient supported on the support surface.

18. The patient support apparatus of claim 1 wherein the remote network service forwards information to the patient support apparatus that controls at least one circumstance under which the computer should issue an alert.

19. The patient support apparatus of claim 1 wherein the computer is further adapted to receive from the remote network service a movement tracking algorithm, the computer using the movement tracking algorithm for tracking movement of a patient supported on the patient support apparatus.

20. The patient support apparatus of claim 1 wherein the computer is further adapted to act as a wireless software access point for the remote network for devices positioned within communication range of the computer, whereby at least one of the devices communicates with the remote network through the computer.

21. The patient support apparatus of claim 20 wherein the devices include smart phones and portable personal computing devices.

22. The patient support apparatus of claim 20 wherein the transceiver follows standards of Institute of Electrical and Electronics Engineers (IEEE) 802.11.

23. The patient support apparatus of claim 22 further including a second transceiver different from the transceiver, the computer adapted to communicate with the at least one of the devices using the second transceiver.

24. The patient support apparatus of claim 23 wherein the second transceiver is a Bluetooth transceiver.

25. The patient support apparatus of claim 20 wherein the computer is adapted to provide Internet access to the devices.

26. The patient support apparatus of claim 1 wherein the computer is adapted to execute an additional application that performs at least one of the following: assesses a bed sore risk of a patient; assesses a fall risk of a patient; determines when a patient may be about to exit the patient support apparatus; generates billing information based on usage of the patient support apparatus; and determines if a patient has turned or not based on the outputs from the load cells.

27. The patient support apparatus of claim 26 wherein the display is incorporated into the patient support apparatus and the remote network service determines at least one item of information to be shown on the display.

28. The patient support apparatus of claim 1 wherein the application communicates with at least one of the following: an electronic medical records service; a caregiver workflow service; an admission, discharge and tracking (ADT) service; a real time location service; and a caregiver communication service.

* * * * *

UNITED STATES PATENT AND TRADEMARK OFFICE
CERTIFICATE OF CORRECTION

PATENT NO. : 9,833,194 B2
APPLICATION NO. : 14/211613
DATED : December 5, 2017
INVENTOR(S) : Michael Joseph Hayes, David Terrance Becker and Annie Désaulniers Page 1 of 1

It is certified that error appears in the above-identified patent and that said Letters Patent is hereby corrected as shown below:

In the Claims

Column 27, Claim 16, Line 34:
"The patient support apparatus of claim 1 wherein the"
Should be:
-- The patient support apparatus of claim 15 wherein the --

Signed and Sealed this
Fifteenth Day of May, 2018

Andrei Iancu
*Director of the United States Patent and Trademark Office*